(12) United States Patent
Gaillard et al.

(10) Patent No.: US 10,512,402 B2
(45) Date of Patent: Dec. 24, 2019

(54) NON-INVASIVE OCCULAR BIOMARKERS FOR EARLY DIAGNOSIS OF DISEASES

(71) Applicant: BOARD OF TRUSTEES OF NORTHERN ILLINOIS UNIVERSITY, Dekalb, IL (US)

(72) Inventors: Elizabeth R. Gaillard, Dekalb, IL (US); Devi Kalyan Karumanchi, Novi, MI (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 154 days.

(21) Appl. No.: 15/557,727

(22) PCT Filed: Apr. 22, 2016

(86) PCT No.: PCT/US2016/028976
§ 371 (c)(1),
(2) Date: Sep. 12, 2017

(87) PCT Pub. No.: WO2016/172576
PCT Pub. Date: Oct. 27, 2016

(65) Prior Publication Data
US 2018/0199817 A1     Jul. 19, 2018

Related U.S. Application Data

(60) Provisional application No. 62/151,234, filed on Apr. 22, 2015.

(51) Int. Cl.
*A61B 5/00*     (2006.01)
*A61B 6/00*     (2006.01)

(52) U.S. Cl.
CPC .......... *A61B 5/0071* (2013.01); *A61B 5/4833* (2013.01); *A61B 5/4842* (2013.01); *A61B 5/7246* (2013.01); *A61B 6/483* (2013.01)

(58) Field of Classification Search
CPC ... A61B 5/0071; A61B 5/4833; A61B 5/4842; A61B 5/7246; A61B 6/483
See application file for complete search history.

(56) References Cited

U.S. PATENT DOCUMENTS

| | | | |
|---|---|---|---|
| 2006/0166879 A1 | 7/2006 | Bhushan et al. | |
| 2011/0045597 A1 | 2/2011 | Rao et al. | |
| 2011/0293154 A1 | 12/2011 | Meixner et al. | |
| 2011/0313295 A1* | 12/2011 | Smith | A61B 5/0059 600/476 |
| 2012/0078075 A1* | 3/2012 | Maynard | A61B 5/0071 600/365 |

(Continued)

OTHER PUBLICATIONS

Hammer et al., "Ocular fundus auto-fluorescence observations at different wavelengths in patients with age-related macular degeneration and diabetic retinopathy," Graefe's Arch. Clin. Exp. Ophthalmol., 246(1): 105-114 (2008). (Year: 2008).*

(Continued)

*Primary Examiner* — Jennifer Wecker
(74) *Attorney, Agent, or Firm* — Barnes & Thornburg LLP; Alice O. Martin

(57) ABSTRACT

Materials and methods are disclosed for screening advanced glycation end-products from the mammalian ocular lens proteins to quantify early biomarkers for the diagnosis of diabetes mellitus and related complications.

8 Claims, 28 Drawing Sheets

Specification includes a Sequence Listing.

(56) References Cited

U.S. PATENT DOCUMENTS

| | | | |
|---|---|---|---|
| 2012/0203086 A1* | 8/2012 | Rorabaugh | A61B 3/1173 600/321 |
| 2013/0196873 A1* | 8/2013 | Wurdinger | C12Q 1/6886 506/9 |
| 2014/0017203 A1* | 1/2014 | Choi | A61K 38/1709 424/93.2 |
| 2014/0093974 A1 | 4/2014 | Lopes-Virella et al. | |

OTHER PUBLICATIONS

Grami et al., "α-Crystallin binding in vitro to lipids from clear human lenses," *Exp. Eye Res.*, 81(2): 138-146 (2005).

Hammer et al., "Ocular fundus auto-fluorescence observations at different wavelengths in patients with age-related macular degeneration and diabetic retinopathy," *Graefe's Arch. Clin. Exp. Ophthalmol.*, 246(1): 105-114 (2008).

Search Report and Written Opinion issued in app. No. PCT/US2016/028976 (2016).

\* cited by examiner

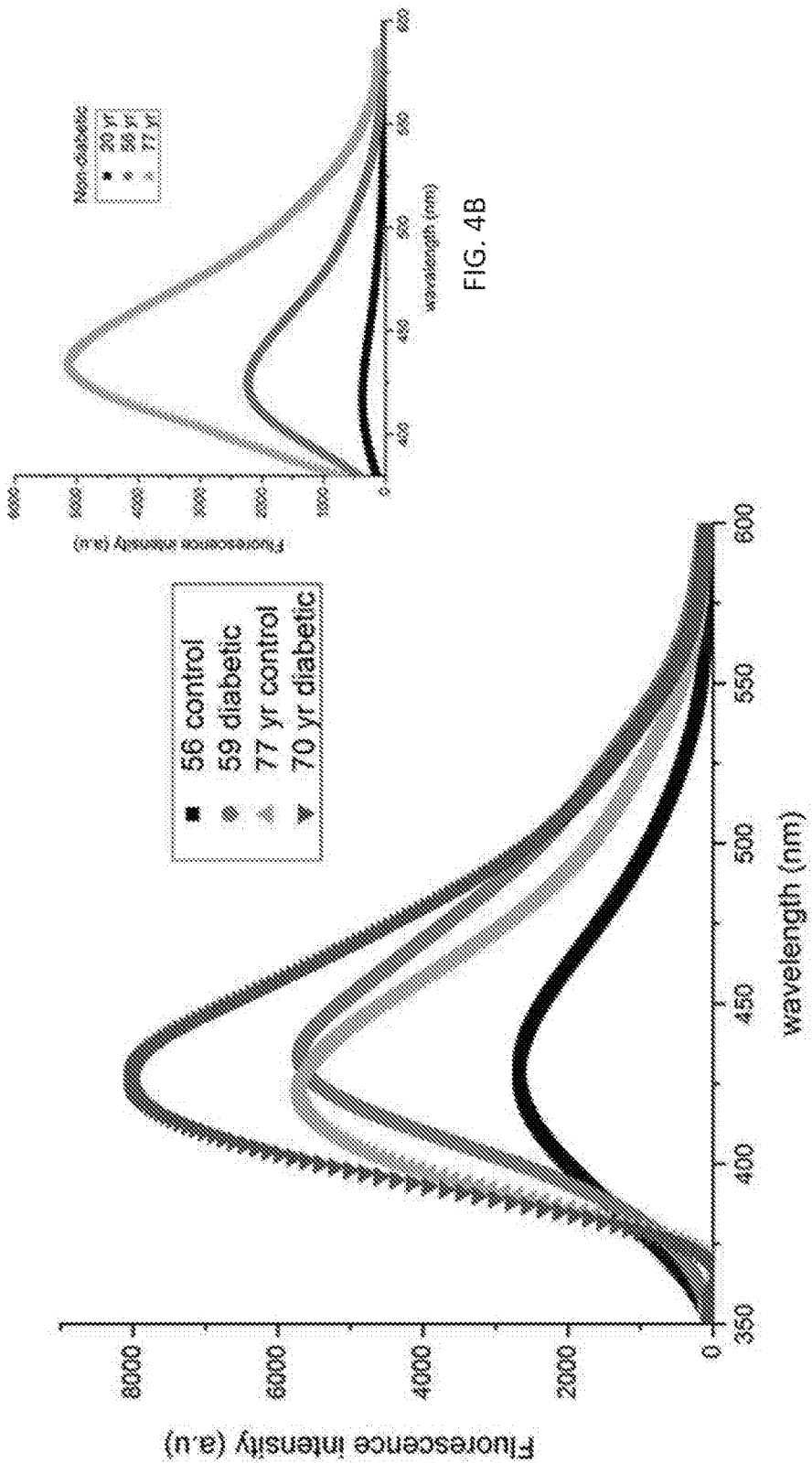

SEQUENCE LISTING

<160> NUMBER OF SEQ ID NOS: 2

<210> SEQ ID NO 1
<211> LENGTH: 173
<212> TYPE: PRT
<213> ORGANISM: homo sapien

<400> SEQUENCE: 1

Met Asp Val Thr Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
            20                  25                  30

Glu Tyr Asp Leu Leu Pro Phe Leu Ser Ser Thr Ile Ser Pro Tyr Tyr
        35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Asp Asp Phe Val Glu Ile
                85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Leu Ser Cys Ser Leu Ser Ala Asp Gly Met Leu Thr Phe Cys Gly Pro
    130                 135                 140

Lys Ile Gln Thr Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170

<210> SEQ ID NO 2
<211> LENGTH: 175
<212> TYPE: PRT
<213> ORGANISM: homo sapien

<400> SEQUENCE: 2

Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
            20                  25                  30

Leu Glu Ser Asp Leu Phe Pro Thr Ser Thr Ser Leu Ser Pro Phe Tyr
        35                  40                  45

```
Leu Arg Pro Pro Ser Phe Leu Arg Ala Pro Ser Trp Phe Asp Thr Gly
    50              55                  60
Leu Ser Glu Met Arg Leu Glu Lys Asp Arg Phe Ser Val Asn Leu Asp
65              70                  75                      80
Val Lys His Phe Ser Pro Glu Glu Leu Lys Val Lys Val Leu Gly Asp
                85              90                      95
Val Ile Glu Val His Gly Lys His Glu Glu Arg Gln Asp Glu His Gly
            100             105                 110
Phe Ile Ser Arg Glu Phe His Arg Lys Tyr Arg Ile Pro Ala Asp Val
        115             120                 125
Asp Pro Leu Thr Ile Thr Ser Ser Leu Ser Ser Asp Gly Val Leu Thr
    130             135                 140
Val Asn Gly Pro Arg Lys Gln Val Ser Gly Pro Glu Arg Thr Ile Pro
145             150                 155                     160
Ile Thr Arg Glu Glu Lys Pro Ala Val Thr Ala Ala Pro Lys Lys
                165             170                 175
```

US 10,512,402 B2

NON-INVASIVE OCCULAR BIOMARKERS FOR EARLY DIAGNOSIS OF DISEASES

CROSS REFERENCE TO RELATED APPLICATIONS

This application is a U.S. nationalization under 35 U.S.C. § 371 of International Application No. PCT/US2016/028976, filed Apr. 22, 2016, which claims the benefit of priority under 35 U.S.C. § 119(e) to U.S. Provisional Application No. 62/151,234, filed Apr. 22, 2015. The disclosures set forth in the referenced applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 21, 2016, is named 253275_SEQ_ST25.txt and is 4,096 bytes in size.

BACKGROUND

Various human diseases and conditions have ocular components. The human eye lens is a transparent, biconvex structure that helps to refract light to be focused on the retinal surface. The change in curvature helps in adjusting the focal distance of the eye so that it can focus on objects at different distances. This adjustment of the lens is called accommodation. Presbyopia is a common ocular condition observed in patients above 50 years and is characterized by loss of flexibility of the crystalline eye lens and in turn, accommodation. Cataract is the leading cause of blindness, affecting 40 million people worldwide. It is a multifactorial ocular disease caused by genetics, age, and environment. There are reports that glycation gradually damages the lens by causing aggregation of the lens proteins.

Diabetes Mellitus

Diabetes mellitus is an endocrine metabolic disorder characterized by high blood sugar levels which give rise to complications in the eye, kidneys and the brain. Diabetes triggers the development of ocular diseases, for example, diabetic retinopathy, glaucoma and cataracts which are the leading cause of blindness around the world. The most common method for the diagnosis of diabetes involves measuring the blood sugar levels in the body. One major disadvantage of this method is that blood sugar levels fluctuate which contributes to false negative results. This leads to delay in treatment, eventually causing permanent damage to the organs. Therefore, diagnosis of diabetes at an early stage is very crucial. Additional or alternative diagnostic tests would be beneficial.

Diabetes arises due to inadequate insulin production, or because the body's cells are non-responsive to insulin, or both. Globally, about 382 million people have diabetes, of which around 46% remain undiagnosed. Diabetes mellitus starts a vicious cycle of diseases affecting the heart, kidneys, eyes and the nervous system. The high blood sugar levels have been observed to cause damage to small blood vessels in these organs by destroying their structure. The total estimated cost of diagnosed diabetes in 2012 is $245 billion which increased to $548 billion in 2013. Overall, the number of diabetics as well as the expenditure including direct and indirect costs have been increasing drastically.

Glycated Proteins

In addition to blood sugar levels, there are several other methods used for the diagnosis of diabetes. Measurement of glycated proteins, primarily glycated hemoglobin (HbA1c or A1C), has been widely used for routine long-term monitoring of glucose control and as a measure of risk for the development of diabetes complications. The A1C test measures average blood glucose for the past 2 to 3 months and, if the values are greater than or equal to 6.5%, the person is considered diabetic. The Fasting Plasma Glucose (FPG) and Oral Glucose Tolerance (OGT) tests measure the blood sugar levels after fasting and having a sweet drink respectively. Values greater than or equal to 126 mg/dl and 200 mg/dl are considered diabetic in FPG and OGT respectively. (Table 7)

Although, these tests give accurate results in diabetic patients, they have their exceptions. The blood glucose levels in the body fluctuate depending on the meals, exercise, sickness, and stress. It has also been shown that different diagnostic tests might give varying results and not agree with one another. The glycation of hemoglobin occurs at several amino acid residues and, as a result, several adducts of hemoglobin A (HbA) and various sugars are formed by the non-enzymatic post-translational glycation process. This process involves the formation of a labile Schiff base intermediate followed by the Amadori rearrangement. The reaction is slow, irreparable, and the reaction rate depends on the ambient glucose concentration. Also, these tests do not take into consideration that the proteins, especially in the vasculature, have rapid turnover and hence are not always the same over time.

HbA1c has been recommended as an accurate and precise marker for diabetes based on advances in instrumentation and standardization. The theory behind the A1C test is that red blood cells live an average of three months. So, if the amount of glycated hemoglobin is measured, results will give an idea of glycation that occurred over the last 3 months. But, research has shown that the lifetime of red blood cells of diabetics is comparatively shorter than that of non-diabetics. This means that the hemoglobin turnover is faster in case of diabetics, and therefore is a major disadvantage for diagnosing the patients in their early stages. Also, it has been reported that people with hemoglobin variants, for example, HbC and HbS have shown false negatives. A false elevated A1C level has been observed in certain clinical situations that affect RBC life span with iron deficiency anemia, high alcohol consumption and hypertriglyceridemia. Other cases which have shown false results include patients with kidney failure and liver disease.

Ocular Proteins

Three major proteins called α-, β- and γ-crystallins are found in the eye lens. The structure, biochemical and physiological properties as well as functionalities of these crystallins have been reported. The monomeric γ-crystallins are globular and the smallest with a molecular weight of about 20 kDa. In the case of β-crystallins, their subunits form oligomers with low molecular weight species ($\beta_L$-60 kDa) and high molecular weight species ($\beta_H$-160 kDa). α-crystallin is the most abundant and largest of the lens proteins (~18 nm in diameter) consisting anywhere between 30-40 subunits with molecular weight ranging from 800-1200 kDa.

Due to a very low protein turnover, crystallins are considered to be some of the longest-lived proteins in the human body. Because of the long half-life, α-crystallin is prone to irreversible modifications leading to changes in structure and function. The most commonly observed post-translational modifications include photo-oxidization, deamidation, racemization, phosphorylation, acetylation, glycation and age-dependent truncation. Post-translational modifications alter protein-protein interactions and subsequently destabilize and reduce the solubility of native crystallins.

Alpha-Crystallins

The eye lens is avascular and constitutes a dense matrix of closely packed proteins. α-crystallin is a major water soluble small heat shock protein (~45%) found in the eye lens. It is isolated from vertebrate eye lens as a polydisperse, hetero-oligomeric complex of approximately 800-1200 kDa, consisting of 35-40 subunits. It is made up of two distinct sub-units—A and B in the ratio of 3:1 respectively. It has a chaperone function, protecting other proteins and crystallins from thermal aggregation. This in turn helps in maintaining the transparency of the eye lens. Recently, it has been observed that α-crystallin sub-units are not restricted to the eye lens, but also are expressed in other non-lenticular tissues like retina, heart, brain and kidneys. While αA is mostly restricted to the lens and retina, it has been reported that αB subunit is expressed ubiquitously in cells undergoing stress.

In its native form, α-crystallin consists of two homologous subunits showing 55% sequence similarity in a ratio of 3:1—αA and αB, with 173 and 175 amino acid residues, respectively. The molecular weight of these two subunits is approximately 20 kDa. αA crystallin is confined to the lens with a small amount in the retina, spleen and thymus. αB crystallin is ubiquitously present in the lens, retina and the heart abundantly, and is expressed under stress and pathological conditions in the spinal cord, muscles, brain and the kidneys. There are reports that α-crystallins act as anti-apototic regulators and prevent apoptosis under stress conditions, thereby protecting the tissues from damage A recent study has detailed how in concentrated suspensions of alpha crystallin, inter-particle correlations are well described by the structure factor for a hard sphere fluid.

The chaperone function of α-crystallin has been reported to prevent thermal aggregation of other proteins. Over a period of time, α-crystallin undergoes irreversible post-translational modifications of which non-enzymatic glycation is prominent especially in aging and diabetes. As a result, the protein slowly starts losing its chaperone ability and starts to aggregate. Glycation also leads to loss of anti-apoptotic activity of alpha crystallin.

Although α-crystallin has been studied extensively, the quaternary structure of the native protein has not been elucidated. As a result, the location of protein modifications which are a part of disease pathology are not resolved. As the lens is avascular and has no turnover, the modifications that occur in the lens alpha crystallin due to non-enzymatic glycation are permanent. Reducing sugars react with basic amino acids of proteins to form Schiff's bases which undergo rearrangement to Amadori products and finally form advanced glycation end-products (AGEs). These AGEs lead to loss of protein integrity, increase hydrophobicity and play an important role in protein denaturation.

Protein denaturation is usually associated with the formation of aggregates. Protein precipitation and aggregation involves the growth of large sized particles and hence is an optimum method for biophysical characterization based on particle size. Light scattering characteristics of protein aggregation of crystallin glycation effects on the protein and its role in the decrease of lens flexibility (presbyopia) as well as the formation of cataracts need to be determined.

An important biomarker for diabetes related diseases is the formation of advanced glycation endproducts (AGEs). AGEs are formed due to non-enzymatic glycation of the proteins on exposure to open chain sugars and dicarbonyl intermediates. Hyperglycemic conditions, oxidative and thermal stress lead to the formation of Schiff's bases with basic amino acids like lysine and arginine. Further, Amadori products are formed due to rearrangement of the Schiff's bases when highly reactive carbonyl intermediates accumulate and attack the amino and guanidine groups on the proteins. Unlike hemoglobin and albumin, the heat shock proteins have long half-lives and very low turnover. As a result, the accumulation of glycation products over a long period of time is likely of quantitative significance.

Methylglyoxal (MGO) is a glycating agent that is generated non-enzymatically from the oxidation and spontaneous dismutation of intermediates in the glycolysis pathway or enzymatic oxidation reaction catalyzed by peroxidases. MGO is reported to be toxic and to interfere with cellular mechanisms. It has been reported to impair functions of mitochondria and also produce reactive oxygen species. Another source of this dicarbonyl reactive intermediate in the body is deficiency of triose phosphate isomerase leading to elevated dihydroxyacetonephosphate (DHAP) levels observed in congenital hemolytic anemia and other neurodegenerative diseases. DHAP spontaneously disintegrates to methylglyoxal which acts as a strong agent in the formation of advanced glycation end products (AGEs). Because MGO reacts rapidly with the proteins, modification by MGO is a good in vitro model for investigating the long term effects of glycation on heat shock proteins. (FIG. 17)

SUMMARY

By screening the changes in the ocular lens proteins and, consequently, the intact lens, non-invasive spectroscopic biomarkers were identified for the early diagnosis of diabetes mellitus. The appearance of these biomarkers will indicate commencing a treatment regimen, thereby preventing further complications.

Steady state and time resolved fluorescence measurements were used to study the spectroscopic changes in α-crystallin with increase in time of glycation, in intact lenses from diabetic and nondiabetic donors. A noninvasive diagnostic tool for early detection of diabetes mellitus is disclosed.

A method for diagnosing a disease by non-invasive scanning of the ocular cells and tissue, primarily from the lens, includes:
 (a) detecting fluorophores that formed in the ocular cells and tissue by steady state fluorescence and recording results;
 (b) using the results of the steady state fluorescence detection of (a) to determine the emission maxima;
 (c) quantifying the fluorophores using time resolved fluorescence for determining the fluorescence lifetimes of the fluorophores; and
 (d) using the fluorescence lifetimes to distinguish between normal and pathological ocular cells and tissue.

Ocular disorders include those related to diabetes mellitus. Non-enzymatic glycation-induced structural damage in alpha-crystallin was investigated using biophysical and spectroscopic characterization. Non-enzymatic glycation of proteins for example by MGO, leads to formulation of AGEs and aggregation. Correlations between the structured, molecular and spectroscopic changes in the glycating agent methylglyoxal (MGO) as it slowly denatures due to aggregation induced by non-enzymatic glycation, is a model for the effects of aging and diabetes.

Aspects of the disclosure also relate to a method for diagnosing an ocular disorder or disease by screening the spectroscopic changes with aging and pathological conditions in the eye where the tissue includes a combination of cornea, lens, vitreous and the retina.

Fluorophores are formed on the small heat shock lens proteins, for example, alpha crystallin. The fluorophores include specifically advanced glycation end-products (AGEs) when measured in vitro. When measured in vivo, the fluorophores include a combination of advanced glycation end products formed on macromolecules in the eye. The products include A2E, lipofuscin, FAD, NADH and any other fluorophores formed due to aging and/or pathological conditions in the eye.

A system for diagnosing an ocular disease includes quantifying the spectroscopic changes in the visible spectrum between 401-600 nm based on fluorescence lifetimes with aging and pathological conditions, in the small heat shock protein, alpha crystallin and its sub-units.

An apparatus for detecting fluorophores in an ocular cell or tissue includes means for focusing an excitation light beam on the ocular cell or tissue; means for detecting a fluorescent light emitted from the cell or tissue in a one or more wavebands, wherein the detection means is operable to produce an intensity of fluorescence from the cell or tissue; means for calculating the intensity of fluorescence for each waveband, wherein the calculation means discerns the detection of the fluorophore in the cell or tissue; means for measuring the fluorescence decay with time after a short excitation pulse from the cell or tissue in the specific waveband; means for calculating the fluorescence lifetimes from the fluorescence decay curves using global 1-4 three exponential fitting analysis.

The fitting analysis is assessed based on good autocorrelation function around zero, weighted number of residuals randomly distributed between +3 and −3, reduced chi square values between 0.9-1.1 and Durbin-Watson parameters of greater than or equal to 1.6, 1.7 and 1.8 for one, two and three exponential decay respectively.

An in vitro diagnosis for distinguishing the normal ocular tissue from pathological tissue is based on the fluorescence intensity and lifetime measurements at specific excitation wavelengths between 280-600 nm, and the damage to the proteins in the tissue are confirmed based on X-ray scattering.

The disclosed methods alone or in combination are useful in artificial intelligence, diagnostic, biotechnology, veterinary and forensic applications.

BRIEF DESCRIPTION OF THE DRAWINGS

FIG. 4A. Comparison of steady state fluorescence measurements at an excitation wavelength of 340 nm between non-diabetic (56 and 77 yr old) and diabetic (59 and 70 yr old) human donor lenses. FIG. 4B. In the inset, comparison of steady state fluorescence measurements at an excitation wavelength of 340 nm from non-diabetic human lenses from donors—20, 56 and 77 year old at the time of death can be observed. (Emission maxima 420-430 nm).

FIG. 15. is graphical abstract of diabetic versus non-diabetic tissues, FIG. 15A. is from a 46 year old non-diabetic donor lens.

DETAILED DESCRIPTION

Figure 1:
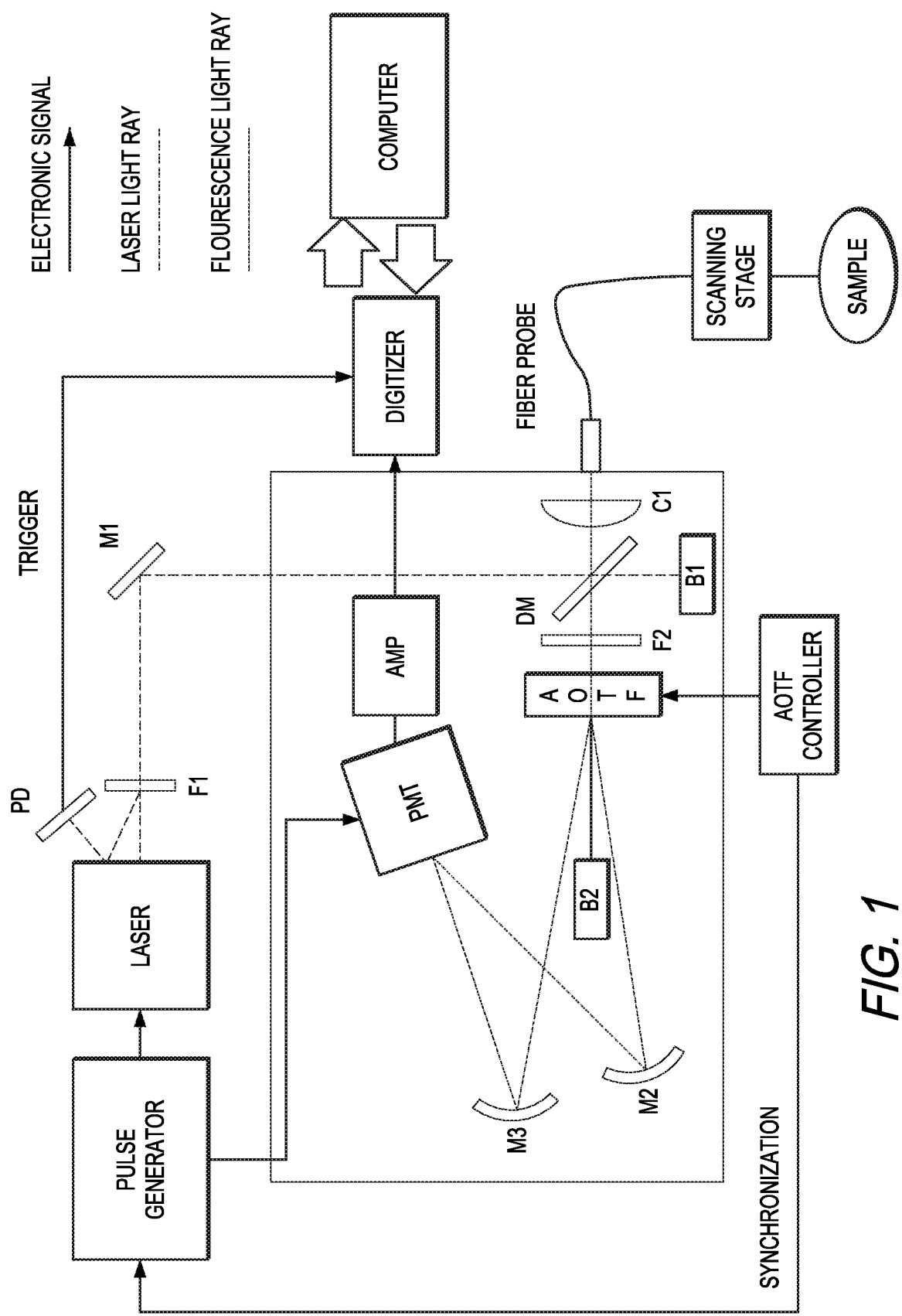
FIG. 1. is a diagrammatic representation of a prototype instrument for the early diagnosis of diabetes using measurements obtained from mammalian eyes.

Physical and chemical biomarkers were sought for the glycolytic modifications in the ocular lens in order to develop a diagnostic tool for the early diagnosis of eye diseases related to other disorders, e.g. diabetes.

The eye lens doesn't have any protein turnover, and therefore is an ideal tissue to study the early stage glycation due to hyperglycemic conditions. By screening for the formation of AGEs and quantifying the resulting physicochemical changes, the development of diabetes may be diagnosed at a very early stage. This in turn, will help in initiating the treatment/precautionary measures from an early stage and prevent the progression of the diseases like diabetic retinopathy and loss of vision.

Lens proteins as well as intact lenses were glycated and the formation of advanced glycation endproducts (AGEs) were characterized using steady state fluorescence and time resolved single photon counting. The biophysical changes in the protein were studied using Dynamic and Static Light Scattering, Small Angle X-ray Scattering to measure the change in scattering intensities.

From the steady state fluorescence measurements, a resonance energy transfer was observed between tryptophan and AGEs. Also, with increase in time of glycation, the AGEs absorbed at wavelengths longer than 370 nm. The fluorescence lifetimes of glycated protein was measured with excitation at 370 nm and emission was monitored at 440 nm using time correlated single photon counting to be around 0.5, 2.8 and 9.8 ns with varying relative contributions. Small angle X-ray scattering data showed the change in inter-particle distances and structural spacing. Dynamic and Static Light Scattering data indicates an increase in particle size, molecular weight and decrease in protein diffusivity. Subsequent measurements were at an excitation wavelength of 340 nm and 435 nm.

One biomarker for diabetes related diseases is the formation of Advanced Glycation Endproducts (AGEs) that result from the Maillard reaction of proteins with glucose α-crystallin in the ocular lens. Glucose α-crystallin is a small heat shock protein with no protein turnover and, consequently acts as a record for post-translational modifications, especially glycation, which forms fluorescent AGEs. Steady state and time resolved fluorescence measurements were used to analyze the spectroscopic changes in alpha crystallin with increase in time of glycation, in intact lenses from diabetic and non-diabetic donors. Overall, the goal was to develop a non-invasive diagnostic tool for early detection of diabetes mellitus.

AGEs are formed due to non-enzymatic glycation of the proteins on exposure to open chain sugars and dicarbonyl intermediates. Hyperglycemic conditions, oxidative and thermal stress lead to the formation of Schiffs bases with basic amino acids, for example, lysine and arginine. Further, Amadori products are formed due to rearrangement of the Schiff's bases when highly reactive carbonyl intermediates accumulate and attack the amino and guanidine groups on the proteins. Unlike hemoglobin and albumin, the heat shock proteins have long half-lives and very low turnover. As a result, the accumulation of glycation products over a long period of time is of quantitative significance.

By screening the changes in the lens proteins and, consequently, the intact lens, non-invasive spectroscopic biomarkers were identified for the early diagnosis of diabetes mellitus. The appearance of these biomarkers will, in turn, act as a standard diagnostic test for commencing the treatment regimen, thereby preventing further complications.

Establishing a correlation between the structural, molecular and spectroscopic changes in a protein as it slowly denatures due to aggregation induced by non-enzymatic glycation, elucidates the importance of a glycation model of aging and diabetes and the pathological mechanisms in various degenerative diseases.

Figure 2:
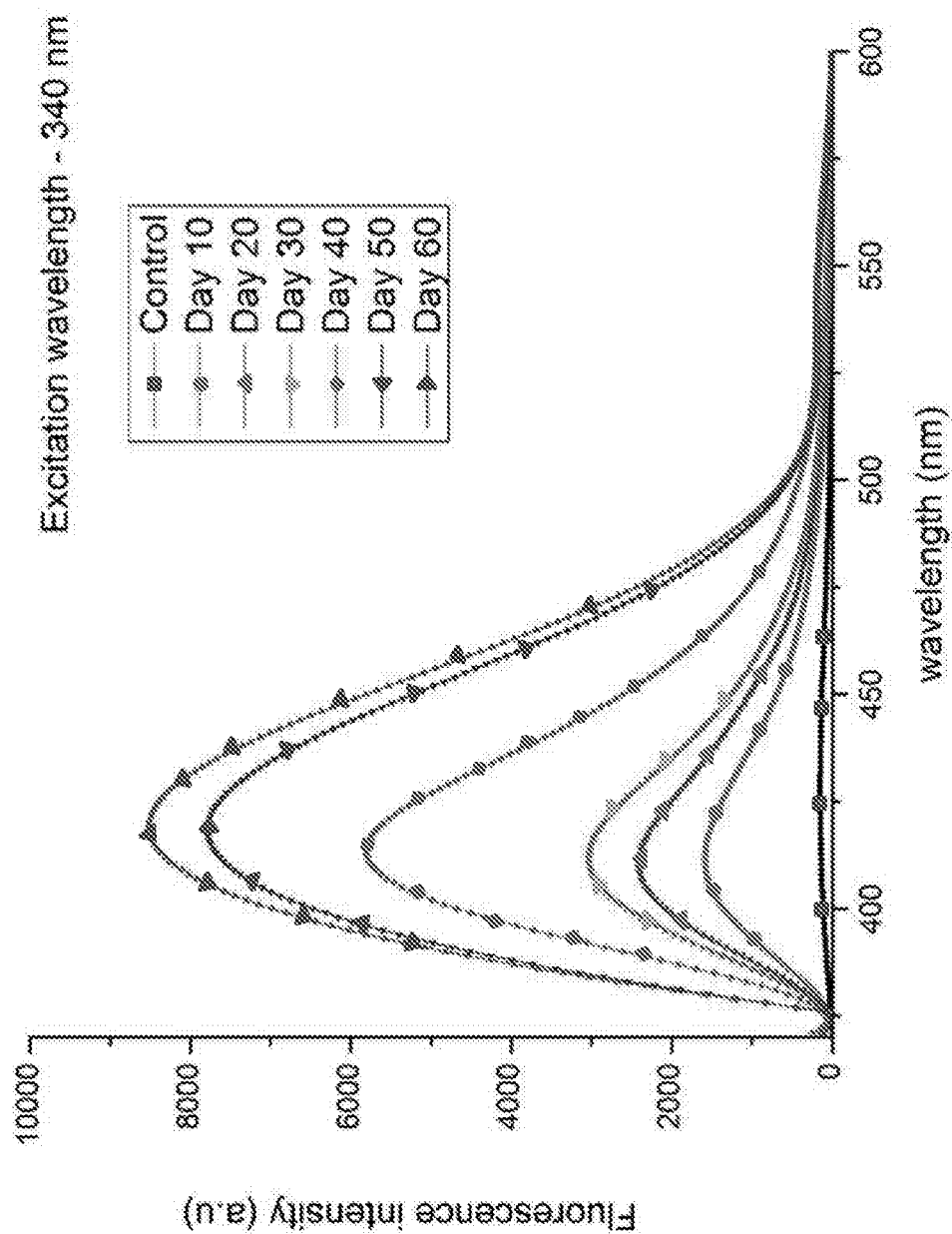
FIG. 2. Steady state fluorescence spectra of α-crystallin with increase in time of glycation at an excitation wavelength of 340 nm.
Figure 3:
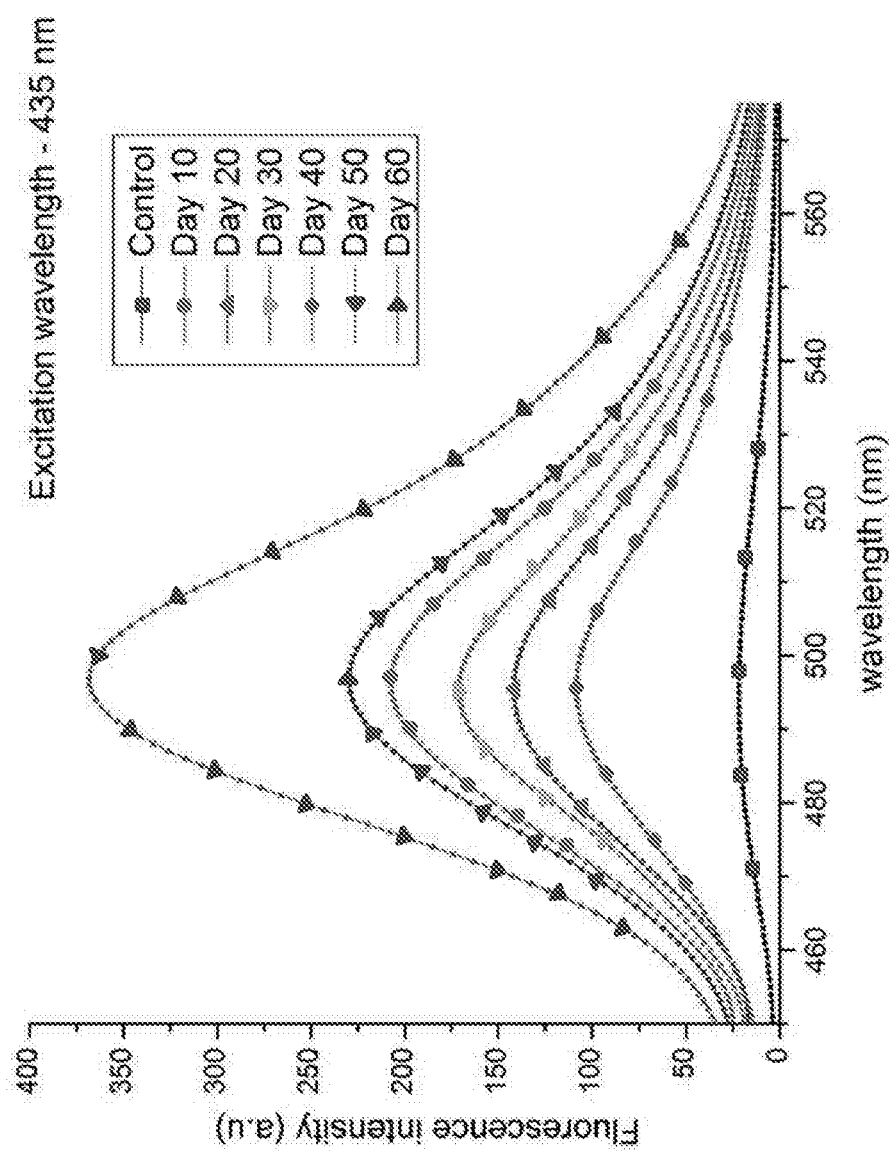
FIG. 3. Steady state fluorescence spectra of α crystallin with increase in time of glycation at an excitation wavelength of 435 nm.
Figure 37:
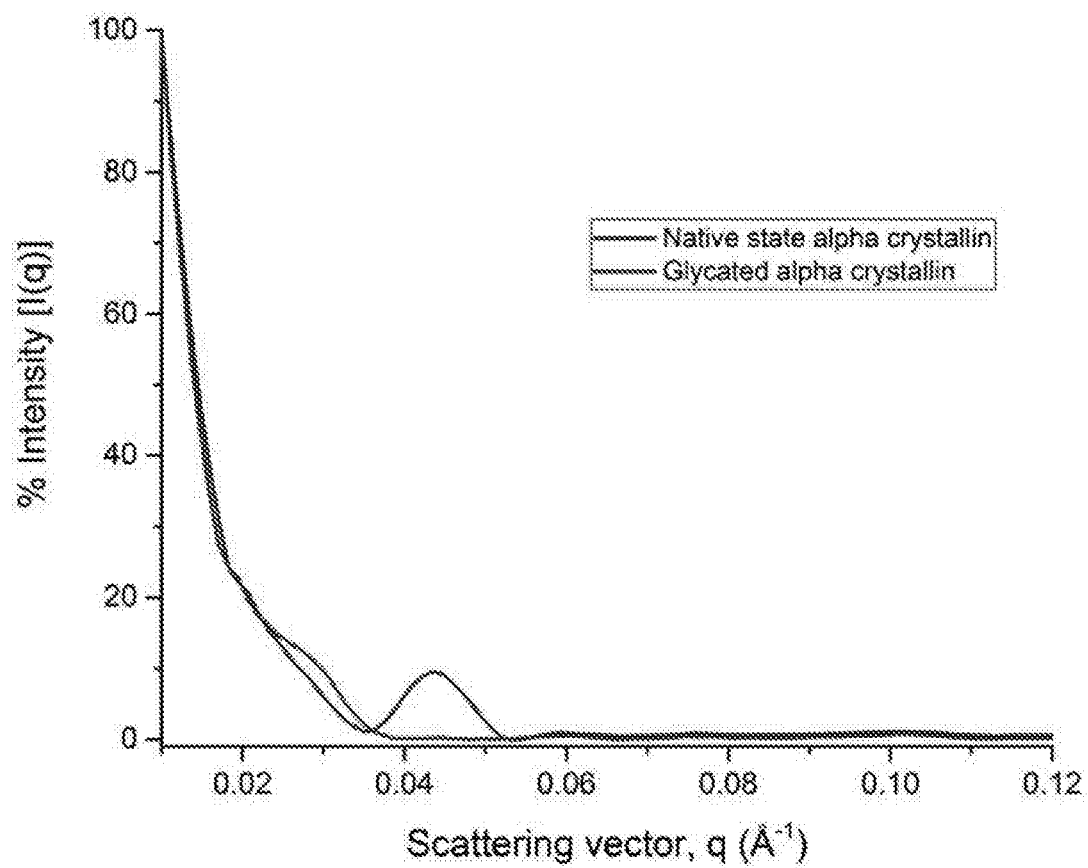
FIG. 37. Small angle X-ray scattering data to measure the inter-particle distances of unmodified and glycated α-crystallin.

Emission spectra were recorded from unmodified and glycated alpha crystallin for the excitation wavelengths set at 340 and 435 nm. By excitation at 340 nm, emission spectra showed one distinct peak (FIGS. 1 and 6) located at about 440 and 460 nm compatible with the absorption caused by AGEs. A broad band was observed at 500 nm by increasing the excitation wavelength to 435 nm (FIGS. 2 and 37). Fluorescence emission spectra were also recorded from intact lenses from donors with and without diabetics. Qualitatively, the shape and peak value of the emission spectra excited at the same wavelength were very similar for α-crystallin and the intact lenses (FIGS. 3 and 4), indicating the fluorophore formation in lens crystallins.

The fluorescence lifetimes of glycated α-crystallin, when excited at 340 and 435 nm can be seen in Tables 1 and 2 respectively. The success of the fit was evaluated using reduced chi-square value and Durbin-Watson parameter. The reduced chi square value was considered good at values between 0.9-1.2. The Durbin-Watson parameter was 1.6, 1.7 and 1.8 or more for a one, two and three exponential decay respectively for successful evaluation of the fit. Similarly, the time resolved fluorescence decay curves from intact lenses at 340 and 435 nm were collected to obtain the lifetimes of the fluorophores as seen in Tables 3, 4, 10-13 respectively.

Time-resolved fluorescence measurements were measured in triplicate and then the fluorescence decay profiles were analyzed assuming that the model followed a multiple exponential fit. In the case of 340 nm excitation, one or two exponential functions did not provide an acceptable fit, as judged by autocorrelation, number of weighted residuals and Durbin Watson parameters. The lifetimes and their relative contributions were determined at excitation wavelengths— 340 as seen in Table 1. Table 2 shows the fluorescence lifetimes, from unmodified and modified α-crystallin at an excitation wavelength of 435 nm.

Here, noticeable trends are observed in the lifetimes with glycation of the protein. In the visible region, unmodified α-crystallin showed no fluorescence and therefore, no lifetimes. However, for glycated α-crystallin, new shorter and longer lifetimes appear with increase in the time of glycation.

For excitation at 340 nm, no change in lifetime was observable with increasing time of glycation but the amplitude, A1, decreased as the amplitudes, A2 and A3, increased. In addition, the ratio A1/A2 is nearly linear with time of glycation and serves as a relative measure of glycation. Table 2 shows the fluorescence lifetimes from unmodified and modified α-crystallin at an excitation wavelength of 435 nm.

Table 3 provides an overall summary of time resolved fluorescence lifetimes obtained at 340 nm from various donor lenses. Table 4 provides an overall summary of time resolved fluorescence lifetimes obtained by excitation at 435 nm from various donor lenses. It can be seen that the distribution of lifetimes and their individual contribution to the total fluorescence at 435 nm excitation wavelength is very different for non-diabetic and diabetic donor lenses. While the younger non-diabetics did not show any fluorescence, older non-diabetics showed one fluorescence lifetime around 4.7 ns. In the diabetic lenses from younger donors, the time resolved fluorescence decay spectra showed a very good fit with a double exponential decay with lifetimes around 4.6 and 17 ns. The decay spectra from older diabetic donor lenses gave a good fit with triple exponential decay with lifetimes around 1.4, 4.5 and 16 ns.

Non-enzymatic glycation of α-crystallin is presented as an in vitro model for aging, diabetes and degenerative diseases.

Alpha crystallin, a small heat shock protein, has been studied extensively for its chaperone function. α-crystallin sub-units are expressed in stress conditions and have been found to prevent apoptosis by inhibiting the activation of the caspase pathway. Non-enzymatic glycation of the protein leads to the formation of advanced glycation end-products (AGEs). These AGEs bind to receptors and lead to blocking the signaling pathways or cause protein precipitation as observed in aggregation related diseases.

Methylglyoxal (MGO) is one of the major glycating agent expressed in pathological conditions due to defective glycolysis pathway. MGO reacts rapidly with proteins, forms AGEs and finally leads to aggregation. Understanding the non-enzymatic glycation induced structural damage in α-crystallin using biophysical and spectroscopic characterization, leads to develop better disease models for understanding the biochemical pathways and also in drug discovery.

Non enzymatic glycation of the proteins is a characteristic feature of aging and diseases like diabetes. This reaction leads to the formation of advanced glycation endproducts on the proteins leading to prolific damage to their structural integrity. Advanced glycation end-products have been shown to exhibit very strong fluorescence as the degree of glycation enhances. The change in fluorescence intensity can serve as a probe to explain the alterations occurring in the native state protein and also provides information on the degree of damage done to the protein.

The augmentation of fluorescence from glycated protein was observed by screening the fluorescence emission by excitation in UV-A region at 340 nm as well as visible region at 435 nm. Oxidative stress, tobacco smoking and weakened detoxification of AGE precursors have also been reported as some of the reasons for increase in AGE production. Another risk factor for high AGE production is a diet with high sugar content. Increased AGE levels have also been observed to be major biomarkers in pathophysiology of various degenerative diseases. Compared to sugars like glucose and sucrose, the dicarbonyl intermediates are much more reactive. The rate of AGE formation depends on the rate of sugar breakdown into highly reactive intermediates like methyl glyoxal which in turn depends on many intrinsic and extrinsic factors like defective glycolysis pathway, enzymatic peroxidation, deficiency of triose phosphate isomerase, smoking and consumption of high sugar diet.

Steady state fluorescence emission spectra were recorded from intact human lenses by excitation at 340 and 435 nm. At 340 nm, the shape and emission maxima were the same in case of non-diabetic lenses but showed a red shift in case of diabetic lenses. However, with increasing excitation wavelength, the peak emission gradually shifted to longer wavelengths. At 435 nm, fluorescence was observed only in the case of lenses from diabetic donors but not in the non-diabetics. Steady state fluorescence measurements give valuable information about the spectral profiles. Fluorescence is dependent on various factors like concentration of the fluorophores, optical density and instrumental parameters which are not constant for all the samples. One disadvantage of using fluorescence intensities as a standard is the possibility of inner filter effect or self-quenching, especially in case of intact lenses where the protein concentration is very high and the concentration of AGEs increases with age and diabetes.

A better and more reliable alternative is to measure the lifetimes of AGE fluorophores. The fluorescence lifetime is an intrinsic molecular property which is independent of concentration, hence, gives a consistent, dynamic depiction of the fluorophores. Measuring the fluorescence lifetimes is valuable as the fluorescence decay occurs at a nanosecond time scale and is highly influenced by the interacting molecules as well as their microenvironments. The time resolved fluorescence decay lifetimes are very specific and also helps analysis of multiple parameters.

At the excitation wavelength of 340 nm, the emission spectra from glycated α-crystallin has shown a red shift of the emission maxima from 420 nm to around 445 nm with increase in extent of glycation. The shift in the fluorescence emission maxima with time has always been attributed to the formation of new crosslinks within the protein which affects its conformation and in turn the orientation of the fluorophores in their micro-environments. The fluorescence decay observed when the excitation wavelength is 340 nm can be fitted to a sum of three exponential functions.

There are various fluorophores which include photo-degradation products of tryptophan like N-formyl kynurenine, anthranilic acid, kynurenine, 3-hydroxykynurenine, harmane and several advanced glycation end-products. Further, evidence shows that AGEs exhibit photosensitizer activity in the UV region leading to the rapid oxidation of tryptophan. All of these fluorophores have very similar, overlapping spectral profiles and hence can be contributing to the increase in fluorescence intensity with the time of glycation. However, fluorescence lifetimes are highly dependent on the quantum yields and the lifetimes obtained from the fit might be from the tryptophan oxidation products.

With excitation wavelength at 435 nm and an emission maxima between 500-510 nm, the influence of tryptophan on the spectral profiles is shown. However, a characteristic difference in the fluorescence intensity was observed between non-diabetic and diabetic lenses which follows the trend observed in unmodified and glycated α-crystallin. By exciting the diabetic lenses at 435 nm, a significant difference in contribution and also an occurrence of new lifetimes was observed. The appearance of new lifetimes with increase in age or disease progression in diabetic lens might be due to the formation of extensive AGE cross-links along with other post-translational modifications.

While, the fundus auto-fluorescence lifetimes are valuable information, these values are dominated by contributions from A2E, FAD and NADH which are characteristic of age related macular degeneration. The auto-fluorescence emission from the crystalline lens itself acts as an obstruction for screening the fundus and leads to decrease in fundus auto-fluorescence (FAF) signal due to back scattering. On the other hand, the fluorescence lifetimes collected from the lens will be primarily from AGE emission without any spectral interference from the connective tissue making it an effective diagnostic tool for diabetes and other diseases associated with AGE formation. The fluorescence lifetimes of glycated α-crystallin was measured as a protein model and similar consistent results were observed in the human donor lenses. The exact chemical nature of the dominant fluorophores when excited in the visible region is examined. Lens auto-fluorescence lifetimes promises to be a very sensitive, noninvasive biomarker for early diagnosis of diabetic eye diseases.

Amplified concentrations of glycating agents in the body cause modifications in glycoproteins as well as heat shock proteins which is a characteristic feature of aging and diseases like diabetes, cancer and Alzheimer's. The incubation of α-crystallin with different glycating agents leads to the formation of aggregates over a period of time which varies between minutes to years. The aggregates are associated with the destruction of native state α-crystallin and formation of AGEs which are initiated by the condensation of basic amino acids and sugars to form Schiff's bases which undergo rearrangement to form Amadori products.

Figures 5A, 5B:
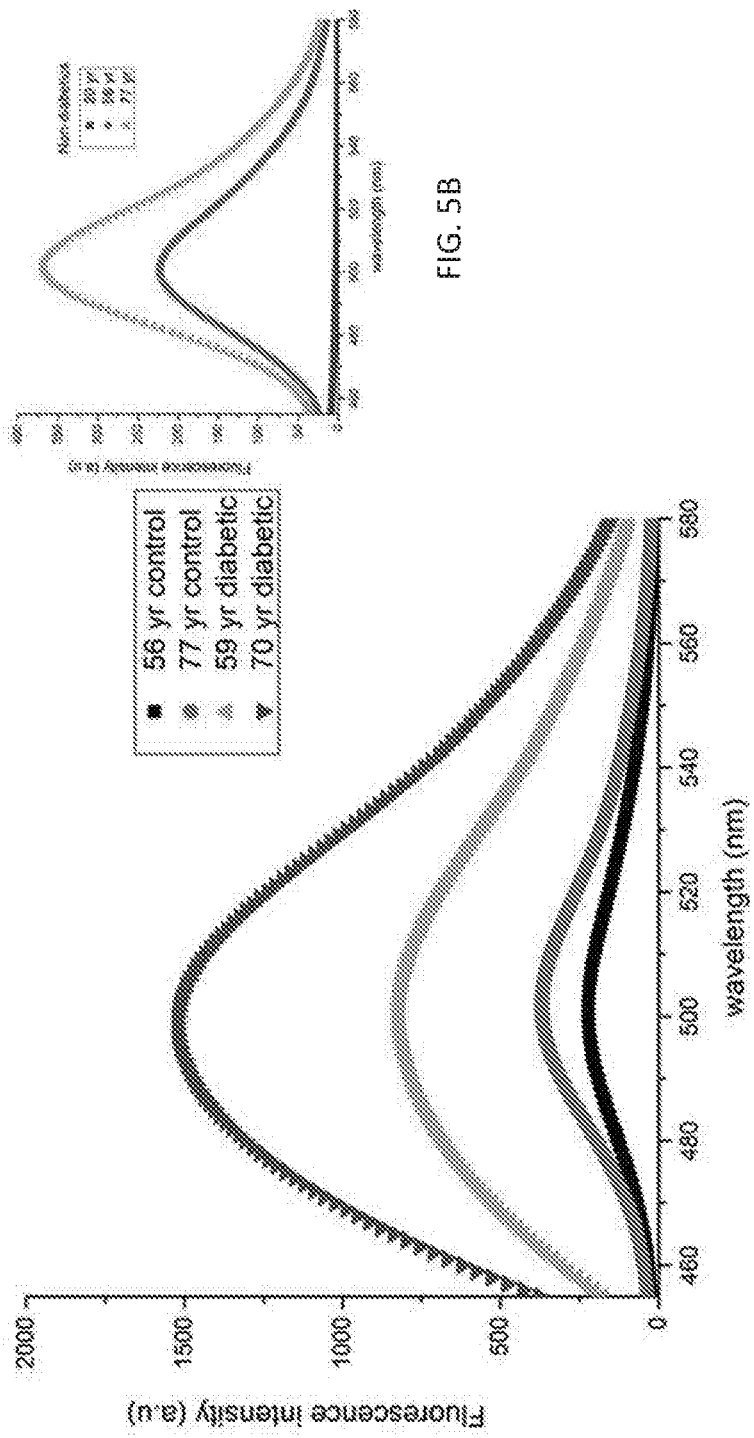
FIG. 5A. Comparison of steady state fluorescence measurements at an excitation wavelength of 435 nm between non-diabetic (56 and 77 yr old) and diabetic (59 and 70 yr old) human donor lenses.
FIG. 5B. In the inset, comparison of steady state fluorescence measurements at an excitation wavelength of 435 nm from non-diabetic human lenses from donors—20, 56 and 77 year old at the time of death can be observed. (Emission maximum 500 nm)

Dynamic Light scattering (DLS) uses visible light to measure the time dependent fluctuations in the scattering intensity to determine the translational diffusion coefficient ($D_T$), and hydrodynamic radius ($R_H$) of a particle. The protein solutions have shown very good light scattering ability and the particle size of native state α-crystallin was found to be 18±2 nm. The reaction with methyl glyoxal was rapid and the particle size of the aggregates was around 350 nm within 9 hours (FIG. 5). With an increase in the particle size, the corresponding diffusivity of the protein decreases. The calculated diffusivity values from the in vitro study measuring the light scattering from the lens and in turn particle size of the aggregates, predicted the formation of a cataract at a very early stage.

Aggregation studies were performed by glycating 1 mg/ml bovine α-crystallin with 1M glucose, 1M sucrose, 0.05 M glycolaldehyde and 10M methyl glyoxal at 25° C. for different time intervals. The change in particle size, hydrodynamic radius, diffusion coefficients and relaxation times of the dilute glycated protein samples were screened using DLS with a HeNe laser at 633 nm as in FIGS. 6, 18-22.

Figure 6:
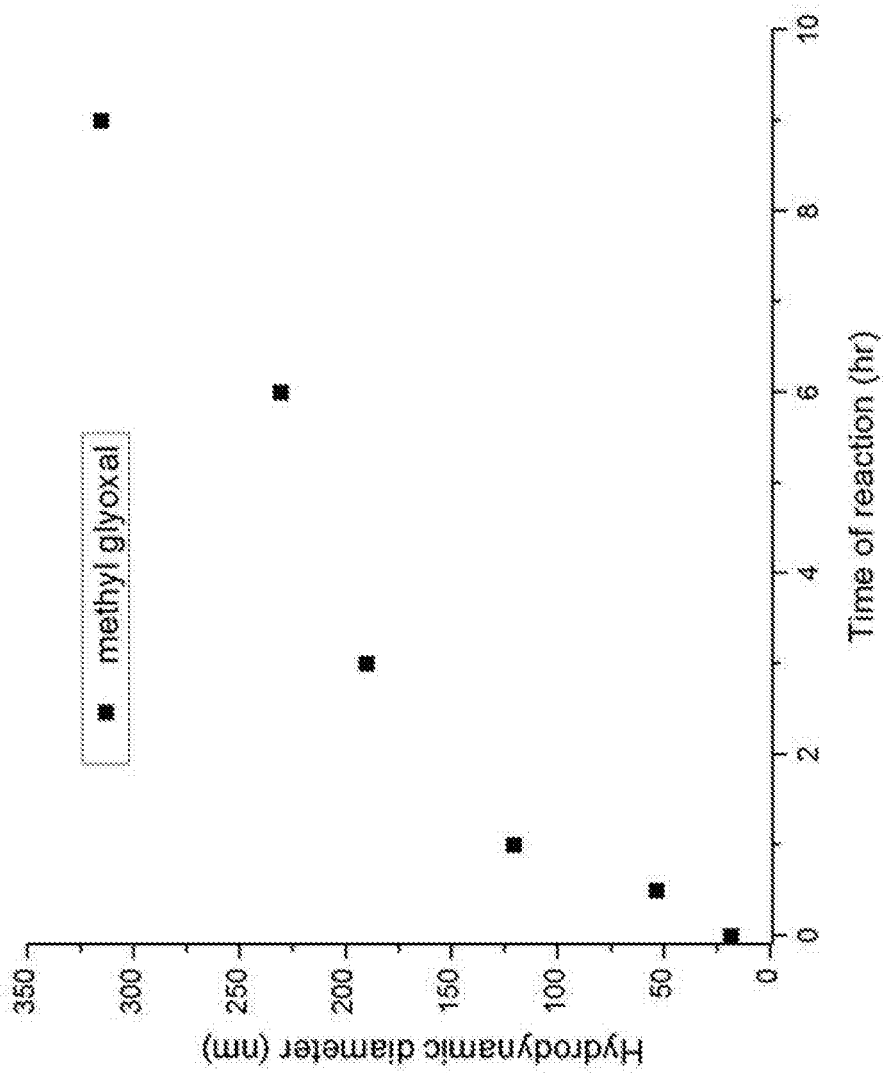
FIG. 6. Increase in hydrodynamic diameter of α-crystallin after incubating with μM methyl glyoxal over a period of 9 hr at 25° C.

Small angle x-ray scattering (SAXS) was used to measure the correlations between alpha-crystallin proteins. SAXS data is very useful in determining the inter-particle spacing providing insight into the packing of α-crystallin in very high concentrations without super-aggregation or crystallization. At low concentrations alpha crystallin shows a monotonic falloff of intensity with scattering vector q. However, for concentrated suspensions there is a peak that appears around q~0.4 $nm^{-1}$ for concentrations of 100 mg/ml and moves out to around q~0.5 $nm^{-1}$ at concentrations around 300 mg/ml with increasing concentration. SAXS was measured from a 250 mg/ml sample of alpha crystallin which showed a strong peak around q=0.42 $nm^{-1}$ (FIG. 6). Upon glycation with 10 µM methylglyoxal the correlation peak diminishes in intensity and moves to smaller q=0.25 $nm^{-1}$. SAXS was measured from a 250 mg/ml sample of alpha crystallin which showed a strong peak around q=0.42 $nm^{-1}$ FIG. 36. Upon glycation with 10 µM methylglyoxal, the correlation peak diminishes in intensity and moves to smaller q=0.25 $nm^{-1}$. This indicates a possible loss of structural integrity of the protein.

Figure 24:
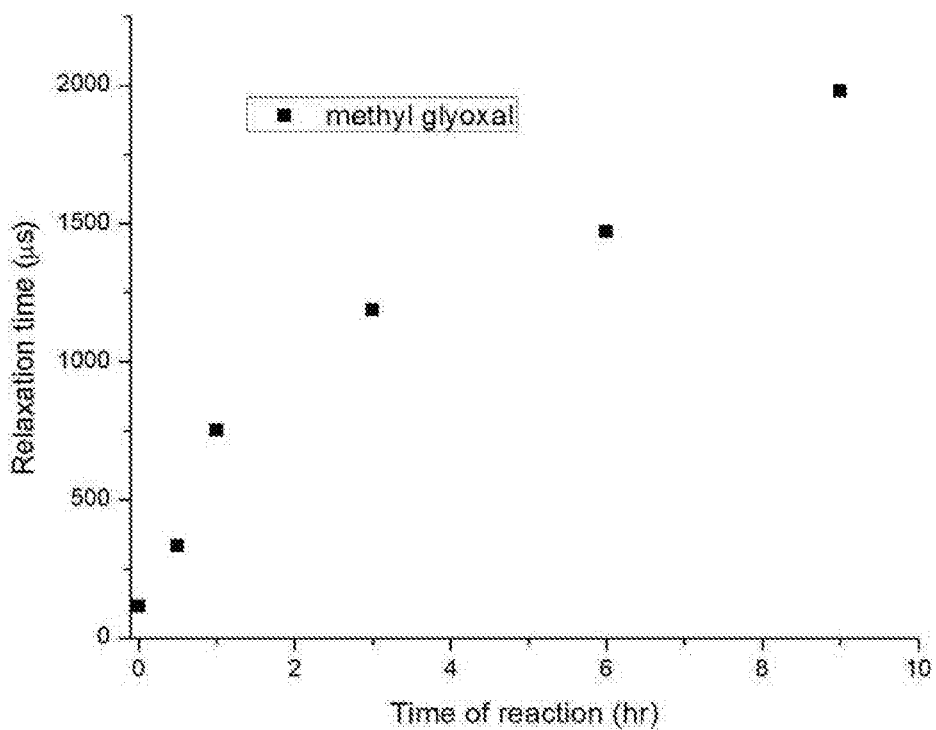
FIG. 24. Change in relaxation times of α-crystallin after incubating with 10 μM methyl glyoxal at 25° C. over a period of 9 hr.

SAXS data is very useful in determining the inter-particle spacing and hence facilitates understanding the packing of α-crystallin in very high concentrations without super-aggregation or crystallization. Previously, it had been reported that concentrated α-crystallin exhibited a spacing of 14.8 nm by measuring the short range interactions. X-ray diffraction patterns from SAXS of native α-crystallin led to reports that the protein exhibits spherical symmetry. Using 250 mg/ml pure α-crystallin has yielded a single reflection pattern at a $Q_{max}$ of 0.042/Å which corresponds to a spacing value of 14.9 nm as shown in FIG. 24. That the peak maxima, also called iso-scattering point, is the same irrespective of the concentration of the protein.

Figure 7:
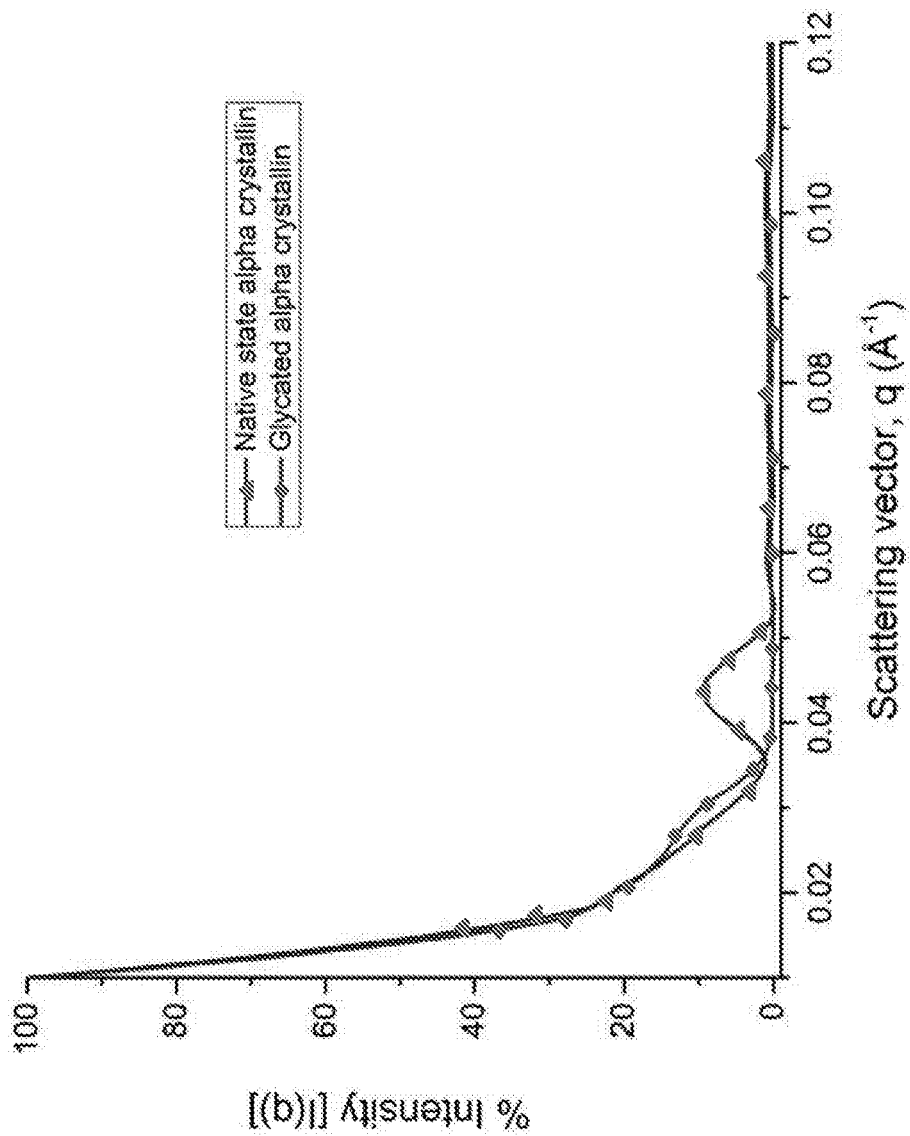
FIG. 7. Small angle X-ray scattering data to measure the inter-particle distances of unmodified and glycated α-crystallin.
Figure 26:
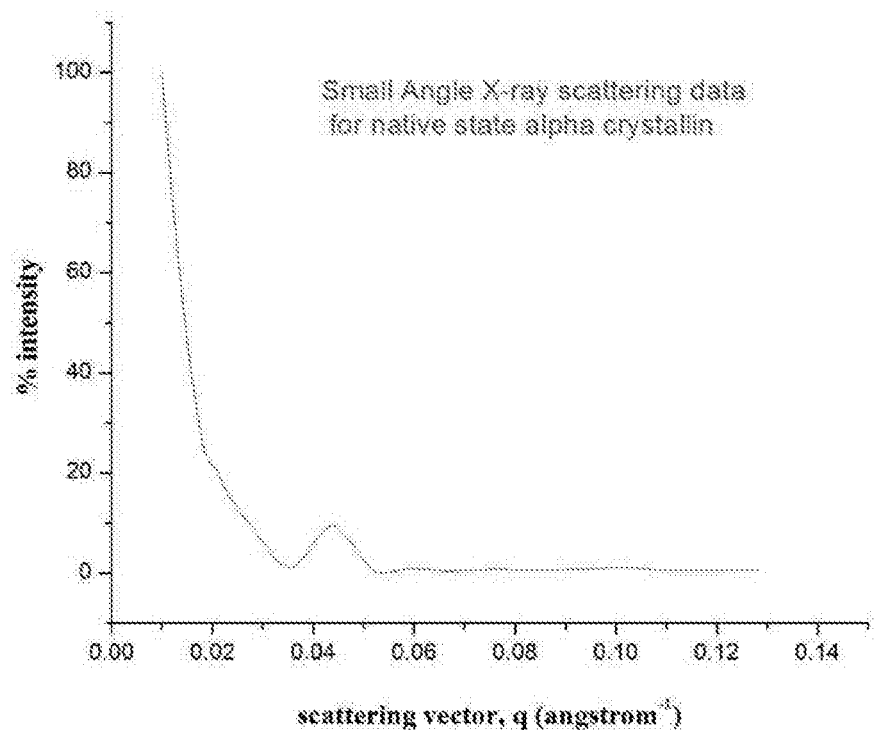
FIG. 26. Small angle X-ray scattering data for measuring inter-particle distances in native state α-crystallin.

The ANS dye is a valuable tool for the detection of protein surface hydrophobicity. Usually, the dye has a low fluorescence yield, which is greatly enhanced on interaction with hydrophobic surfaces. From the experimental data as shown in FIGS. 7 and 26, a conclusion is that hydrophobicity increases with time of glycation. The spectral shape exhibits 2 peaks. This can be explained based on the fact that the fluorescence of ANS dye is highly solvent dependent. So the polarity of the microenvironment affects the emission maxima of this molecule. ANS dye shows an emission maxima around 550 nm in a highly polar environment and a blue shift of around 50 nm in a less polar environment. The native state α-crystallin, upon glycation unfolds to expose the hydrophobic regions to the surrounding polar environment and due to short range interactions, forms aggregates. Previous literature reports that the chaperone ability of methyl glyoxal modified α-crystallin increases initially. However, with increased time of glycation, the protein aggregates, loses its structural integrity and chaperone ability. As a result, other lens proteins are easily prone to stress leading to their damage. Structural studies disclosed here help explain the loss of chaperone activity, thereby establishing the relation between structure and function of alpha crystallin.

Progressive loss of soluble α-crystallin, associated with increased hydrophobicity and formation of aggregates is responsible for increasing the lens stiffness. Heat induced denaturation of α-crystallin may be an important factor in the etiology of presbyopia. However, considering the physiological conditions, non-enzymatic glycation seems to be the main culprit. Cataract and presbyopia can produce myopia due to a change in the refractive index of the crystalline lens of the eye. The presence of high molecular weight aggregates and also advanced glycation end-products lead to a change in both the scattering intensities as well as the spectroscopic properties of the lens. Due to change in refractive index of the lens, the angle of the refracted light changes leading to several focal points in close proximity on the retina causing chromatic aberrations.

Figure 27:
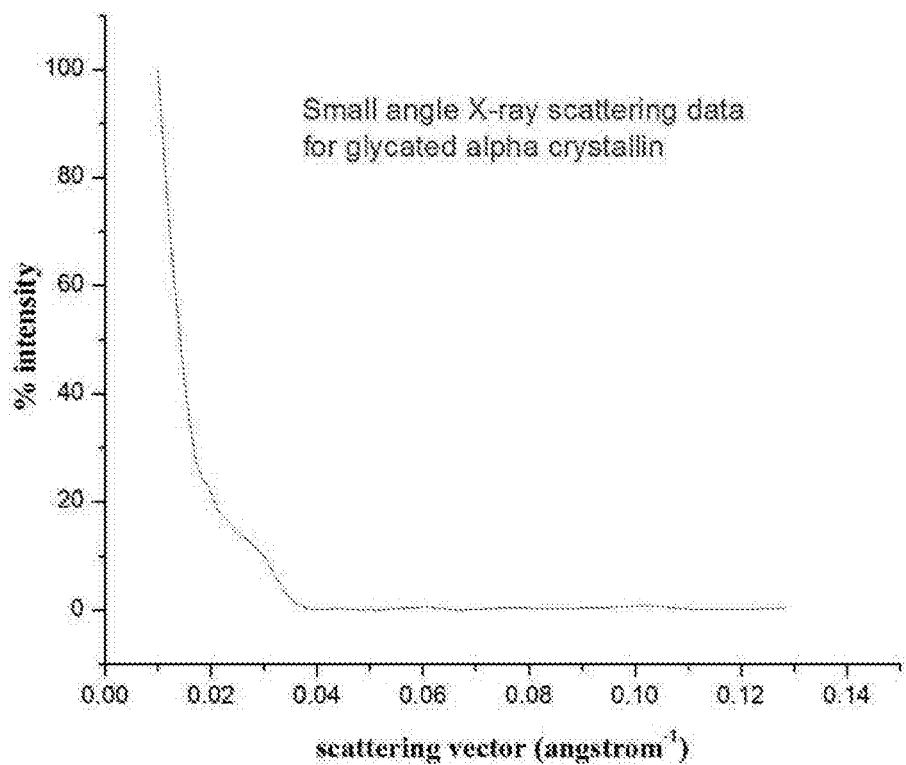
FIG. 27. Small angle X-ray scattering data for measuring inter-particle distances in glycated α-crystallin.

Change in solubility parameters of the lens proteins with increase in time of glycation have been studied by screening the change in water and urea soluble portions using UV-Vis spectrophotometry at 280 nm. FIG. 27 shows that the glycation was associated with significant and progressive insolubility of the lens proteins over the period of time.

Figure 28:
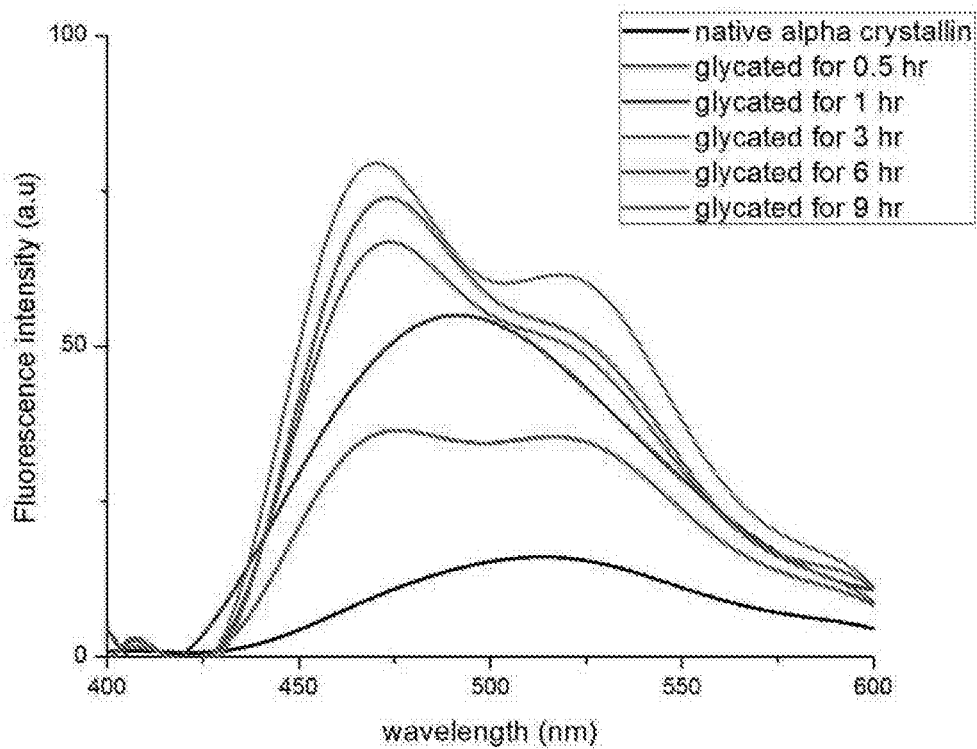
FIG. 28. Change in surface hydrophobicity of the native α-crystallin and 10 μM methyl glyoxal modified α-crystallin over a period of 9 hr at 25° C.

Cataract and presbyopia can produce myopia due to a change in the refractive index of the crystalline lens of the eye. The refractive index of native α-crystallin which is close to that of water also changes as shown in FIG. 28. The presence of high molecular weight aggregates and also advanced glycation end-products leads to a change in both the scattering intensities as well as the spectroscopic properties of the lens. Due to change in refractive index of the lens, the angle of the refracted light changes leading to several focal points in close proximity on the retina causing chromatic aberrations.

Tryptophan has a very strong fluorescence in proteins. The residues which are buried in the hydrophobic core of proteins can have spectra which are shifted by 10 to 20 nm compared to tryptophans on the surface of the protein. Tryptophan fluorescence can be quenched due to microenvironments. The magnitude of fluorescence intensity is a probe to explain the perturbations occurring in the native state. The wavelength maxima of tryptophan fluorescence shifted on modification indicating a change in the microenvironment which was confirmed by surface hydrophobicity measurements (FIG. 7). In α-crystallin, tryptophans are not located at the N-terminus and hence do not have a free amino group to participate in the Maillard reaction. The photo degradation products of alpha crystallin showed that they were primarily from tryptophan oxidation.

Another aspect of tryptophan fluorescence spectral profiles is a shift in the isosbestic point of the spectra. Usually, the presence of an isosbestic point indicates that only two species that vary in concentration contribute to the absorption around the isosbestic point. If a third molecule is participating in the process, the spectra typically intersect at varying wavelengths as concentrations change, creating the impression that the isosbestic point is "out of focus", or that it will shift as conditions change. The reason for this is that the different compounds have varying extinction coefficients at one particular wavelength. Tryptophan oxidation products have spectral profiles similar to AGEs with varying extinction coefficients. This helps explain the decrease in tryptophan fluorescence with increase in the time of glycation.

Figure 8:
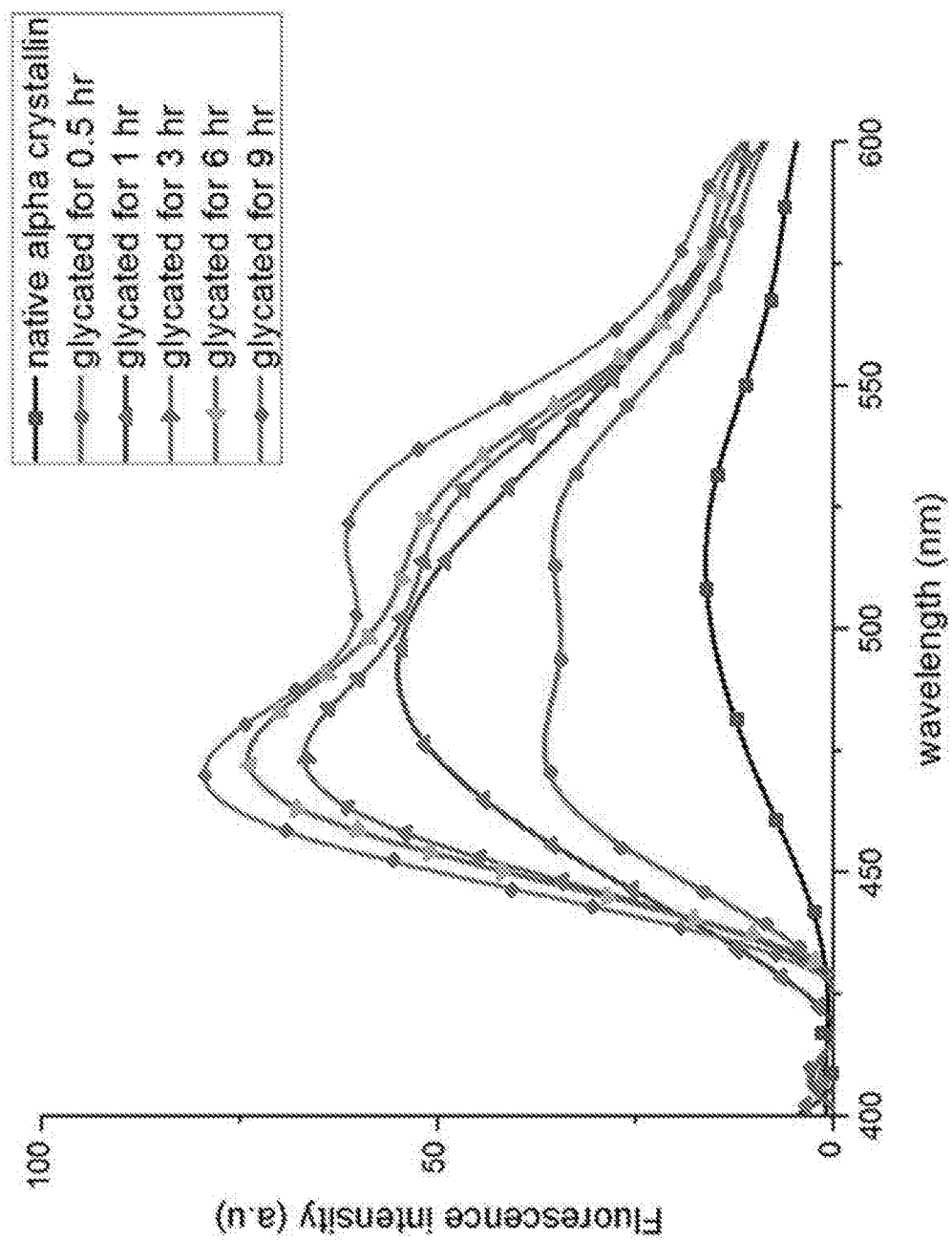
FIG. 8. Change in surface hydrophobicity of the native α-crystallin and 10 μM methyl glyoxal modified α-crystallin over a period of 9 hr at 25° C.
Figure 9:
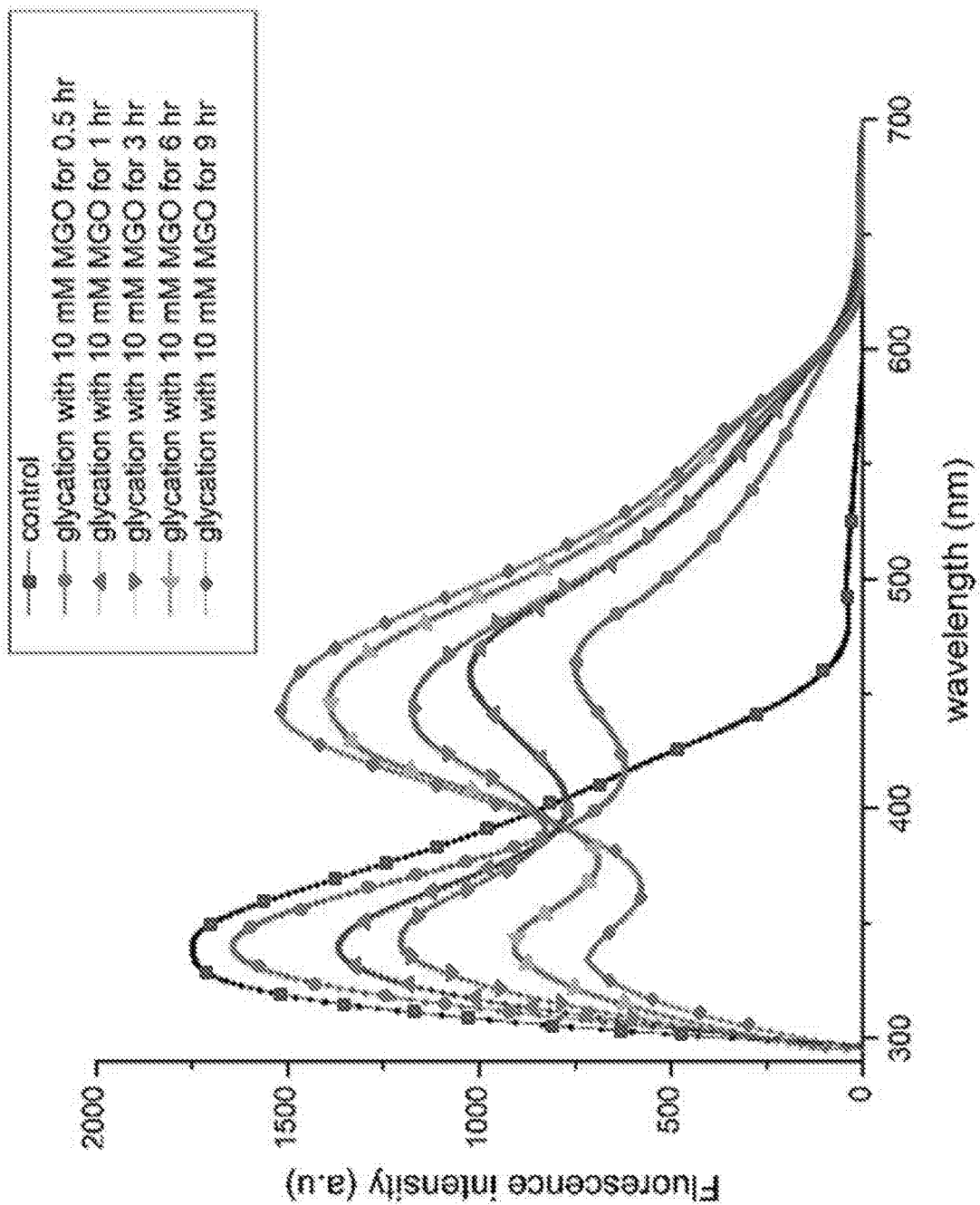
FIG. 9. Change in tryptophan fluorescence of α-crystallin after incubating with 10 μM methyl glyoxal over a period of 9 hr at 25° C.
Figure 10B:
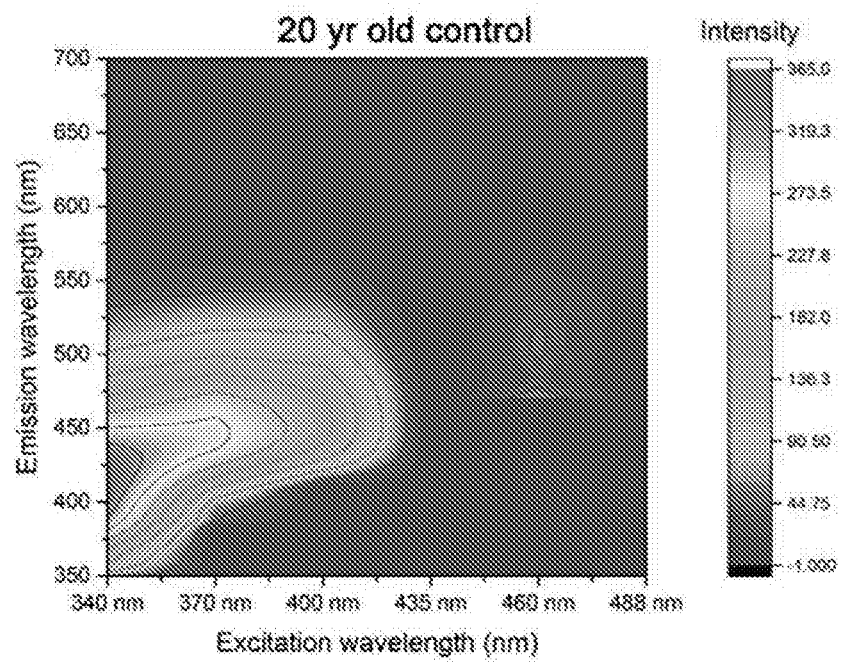
FIGS. 10-12. are photographic comparisons of steady state fluorescence hotspots in matched diabetic and controlled samples.
FIG. 10A. is from a 18 year type 1 diabetic, FIG. 10B. is from 20 year old control.
Figure 10A:
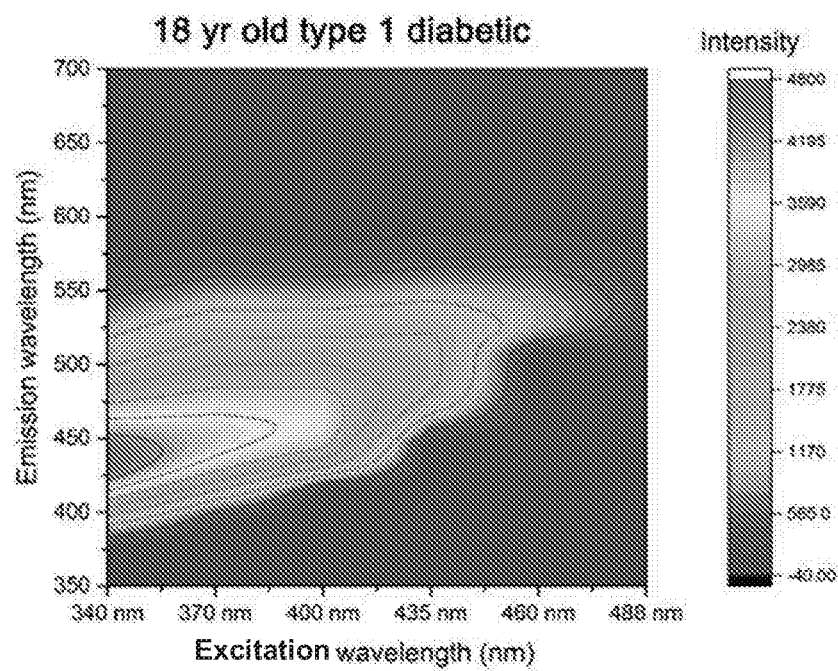
Figure 11B:
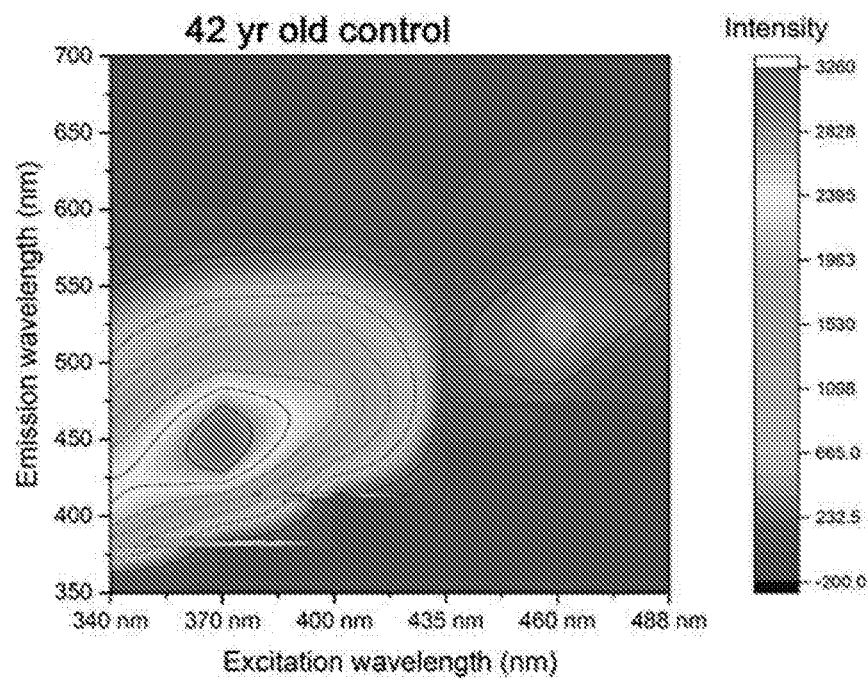
FIG. 11A. is from a 42 year old diabetic, FIG. 11B. is from a 42 year old control.
Figure 11A:
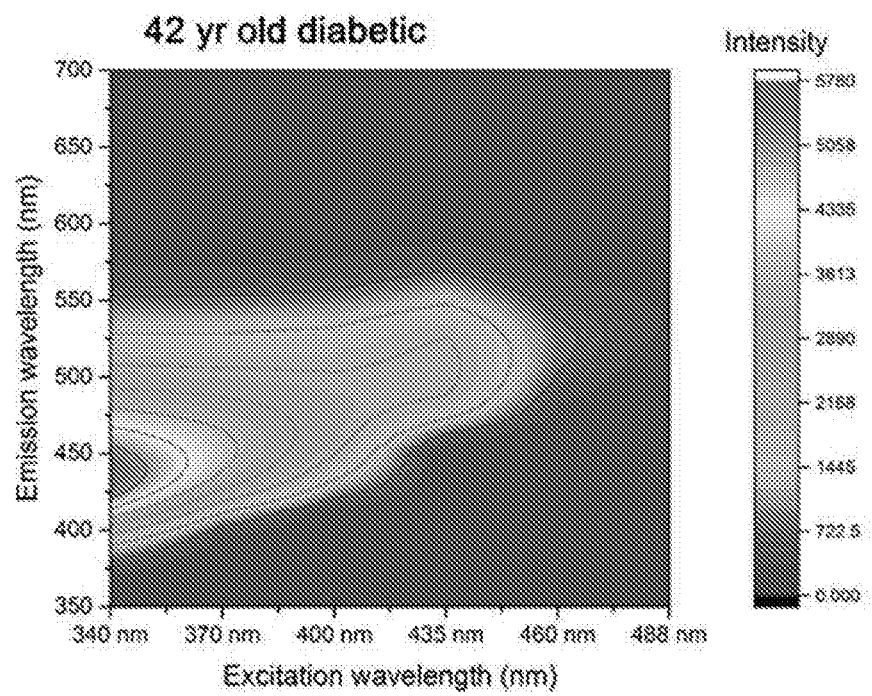
Figure 12B:
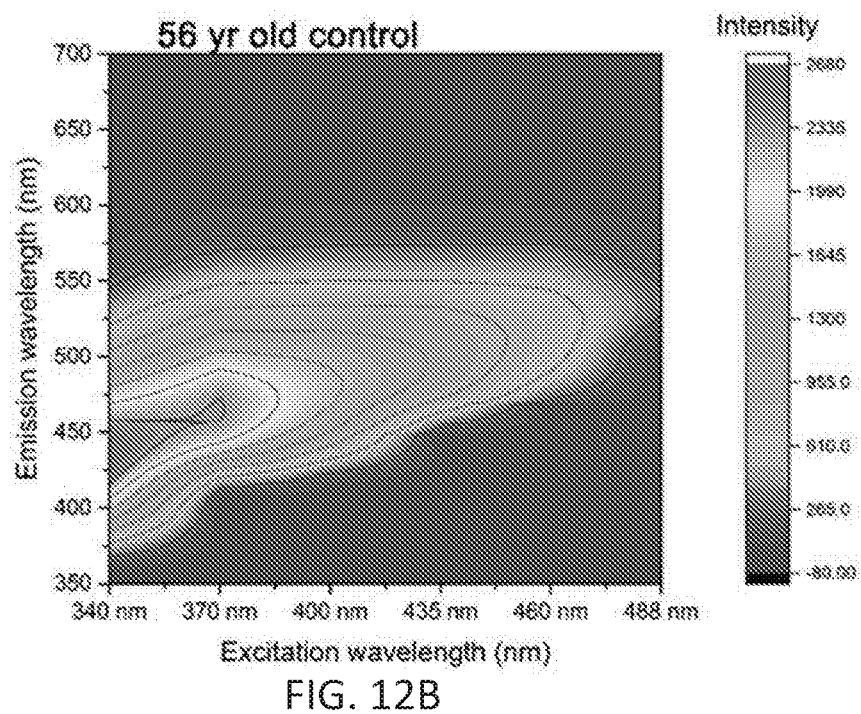
FIG. 12A. is from a 56 year old diabetic with retinopathy, FIG. 12B. is from a 56 year old control.
Figure 12A:
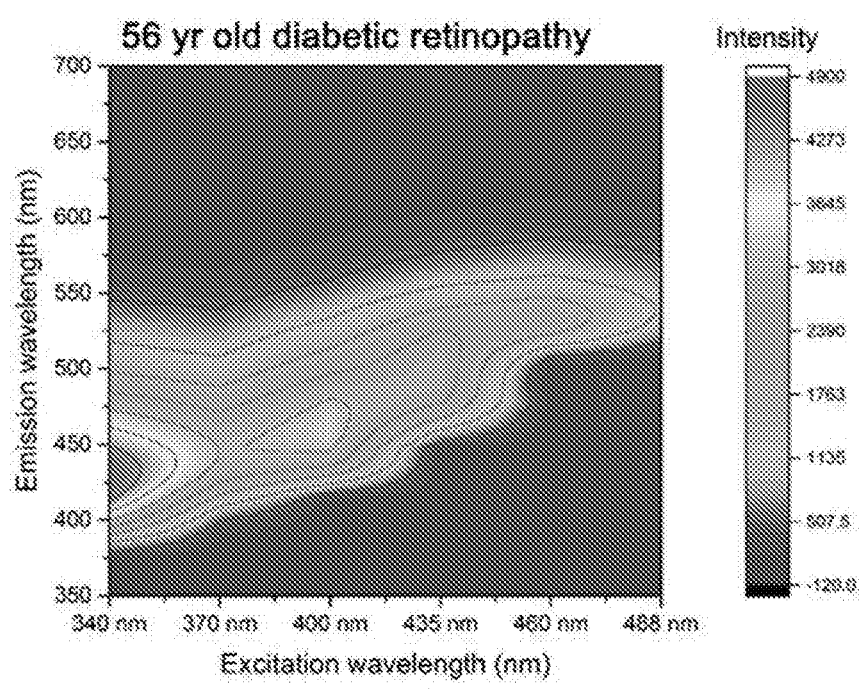
Figure 13:
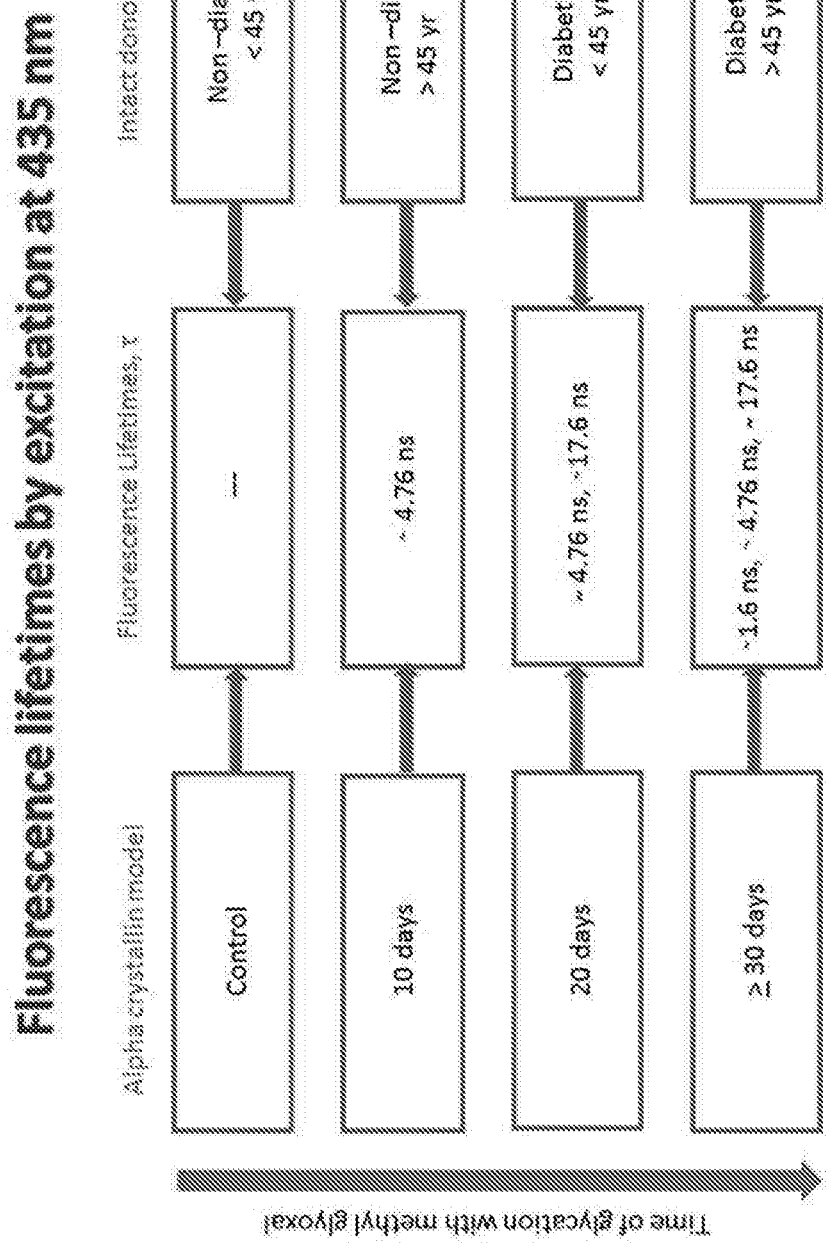
FIG. 13. shows results of fluorescent lifetimes.
Figures 14A, 14B:
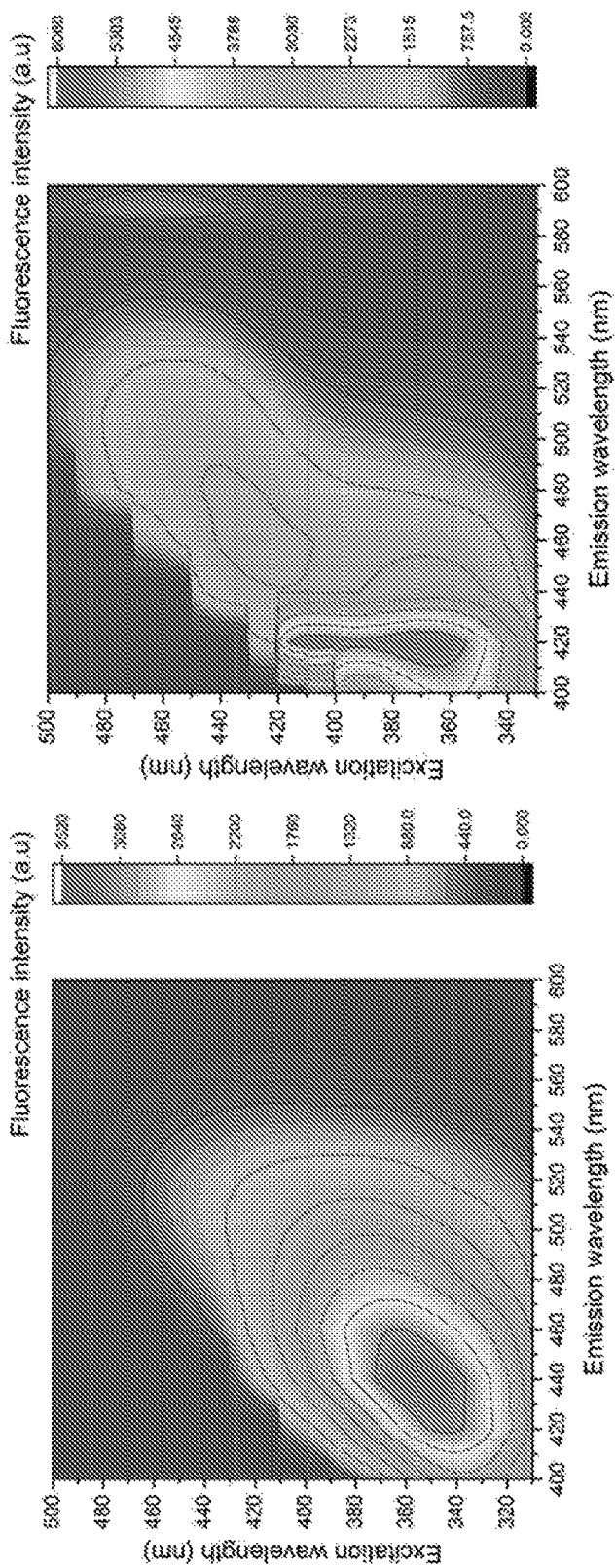
FIG. 14. shows spectral hotspots 14A. in a non-diabetic 46 year old donor, FIG. 14B. in a diabetic 49 year old donor.
Figures 15A, 15B, 15C:
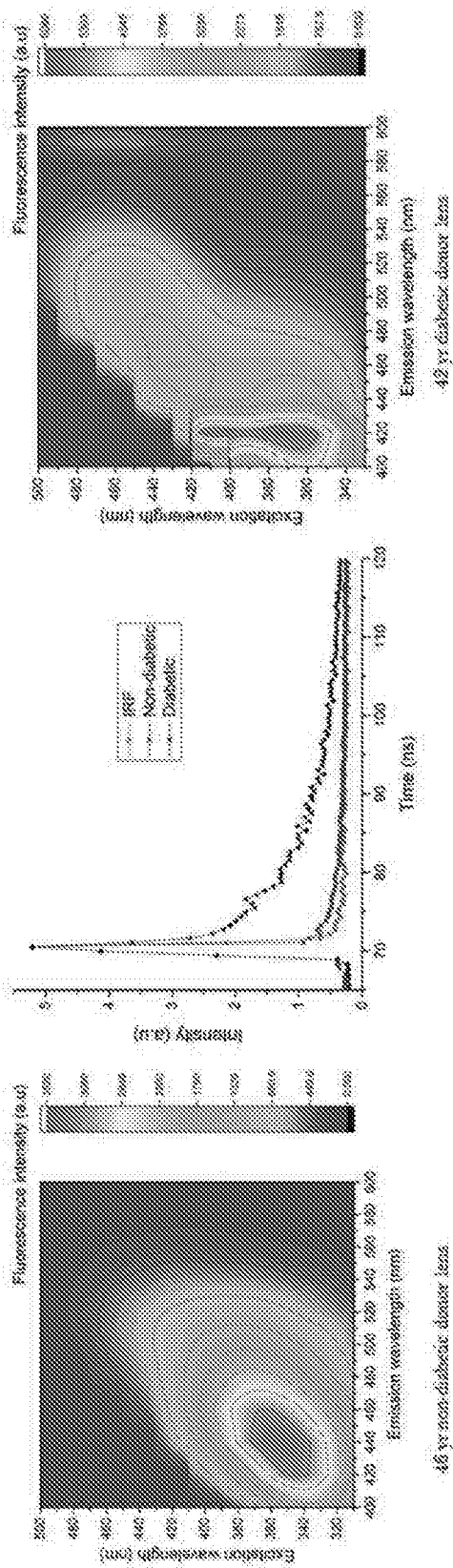
FIG. 15B. time resolved fluorescence graph distinguishing non-diabetic from diabetic lens tissue.
Figure 16:
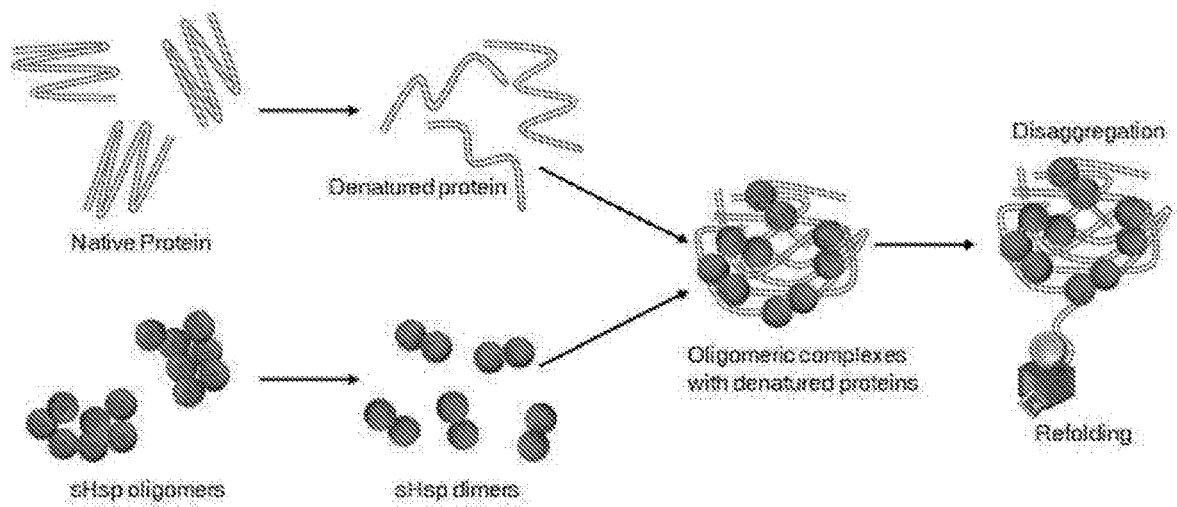
FIG. 16. Mechanism of chaperone action of α-crystallin.
Figure 17:
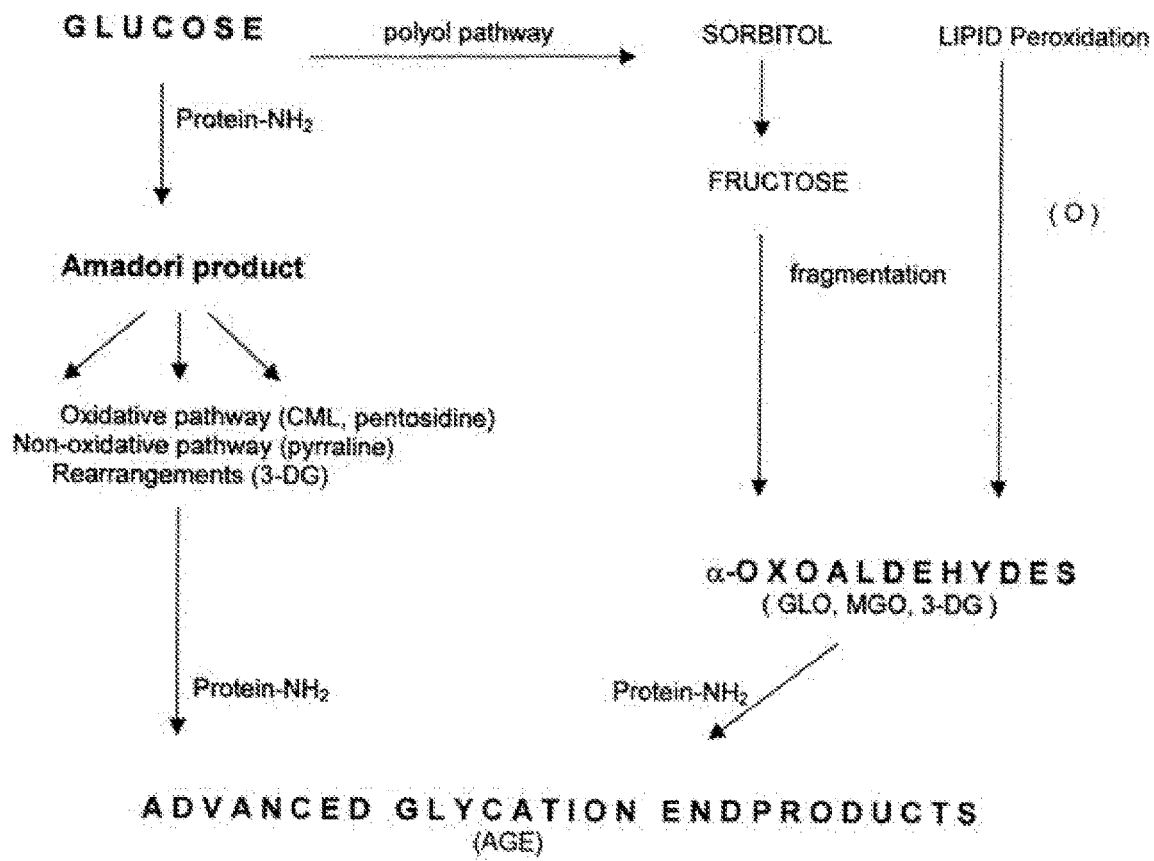
FIG. 17. Non-enzymatic glycation of proteins by simple sugars and dicarbonyl intermediates. (http://www.edb.hr/dialogia.01no2-2.html)

The rate of AGE formation depends on the rate of the formation of highly reactive intermediates due to defective glycolysis pathway and consumption of high sugar diet. The change in AGE fluorescence with decrease in tryptophan fluorescence can be observed in FIG. 8.

Tryptophan (Trp) lifetime measurements can be used to provide information about the changes in the microenvironments. Tryptophan fluorescence is a very valuable tool that can be applied to study folding/unfolding, the effect of environment and solvent exposure on the integrity of the protein. The fluorescence lifetimes of tryptophan can be used to analyze the location of tryptophan and the possibility of short range interactions. The inventors have shown that the fluorescence of α-crystallin is predominantly due to the Trp 9 in both A and B chains while the Trp 60 present in the B chain is buried from exposure. However, after the process of glycation begins, the tryptophans appear to become completely exposed to the surrounding aqueous medium. This can be confirmed from the lifetime measurements as in Table 2, no change were observed in the lifetimes with time of glycation. The tryptophan residues may undergo a shift in their position after once the protein starts to unfold and aggregate leading to the formation of water insoluble residues.

The Trp residues in peptides generally show fluorescence emission spectra, with a peak around the 340-370 nm region, similar to the Trp residues in aqueous media or in fully denatured proteins. However, interaction of peptides possessing Trp residues with proteins would result in diminished exposure of the peptide Trp (as seen in Trp 60) to the aqueous environment with a concomitant blue shift in the fluorescence emission maxima. Simulation studies have shown that, although Trp 60 is exposed to solvent in the α-B subunit, it is buried in the dimer models, located at the interacting interface of the subunits. Using LCMS and isotopic labeling, reports have shown that K70, K88, K92, K99, K103, K145, K150 and K166 are the lysine glycation targets on α-crystallin. R12, R21, R54, R65, R69, R103, R112, R117, R119, R157 and R163 are arginine glycation sites on α-crystallin. Based on these target sites of glycation, modifications may occur within the vicinity of the tryptophan (Trp 60) exposing it to different microenvironments as they are chemically modified.

Figure 23:
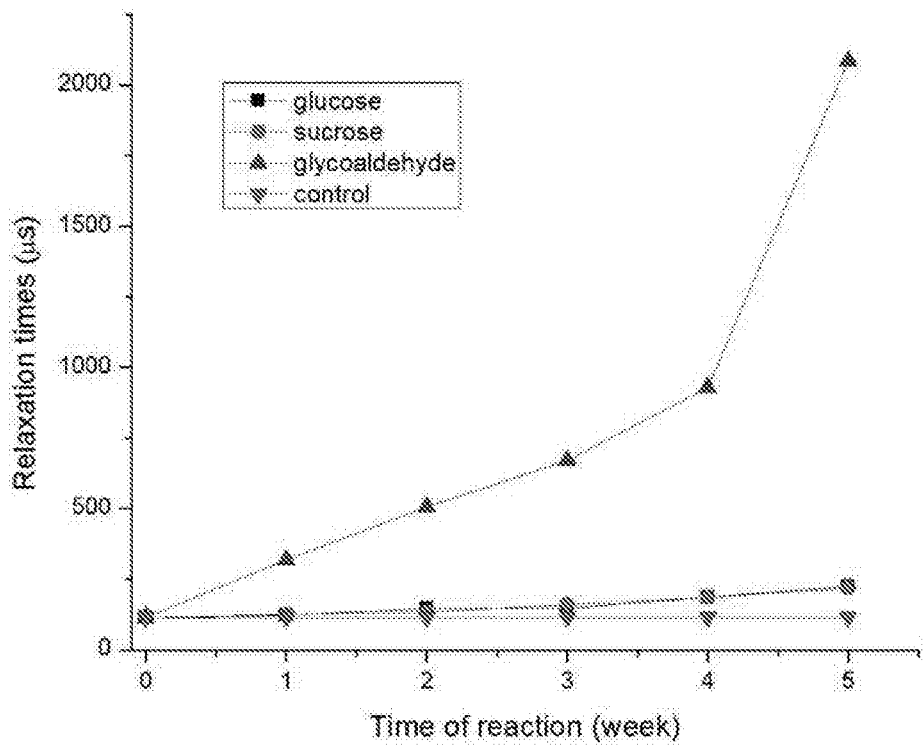
FIG. 23. Change in relaxation times of α-crystallin after incubating with 1M glucose, 1M sucrose and 0.05M glycolaldehyde at 25° C. over a period of 5 weeks.

Approximate molecular masses of modified and unmodified bovine α-crystallin samples were determined using Static Light Scattering (SLS). A Zimm plot was constructed from the light scattering intensities obtained at multiple angles (10, 20, 30, 40, 50, 60, 70, 80, 95, 100, 110 and 120) and different concentrations (0.125, 0.25, 0.5 and 1 mg/ml) to obtain the approximate molecular weights (FIG. 23). Small angle X-ray scattering (SAXS) was used to measure the inter-particle distances as X-rays due to their shorter wavelength can interact with atoms (FIG. 24, 25) and also facilitate understanding the shape of the molecules. These light scattering techniques reveal physical changes in the protein and the effect of modifications on the structure and shape of the protein.

Figure 38A:
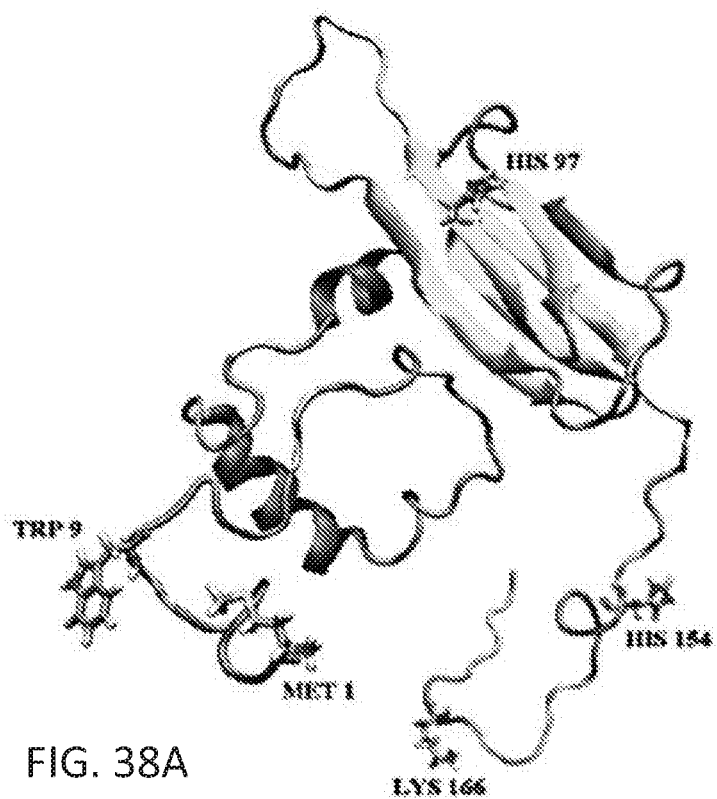
FIG. 38A-B. Positions of several residues in α-crystallin A model and α-crystallin B model.
Figure 38B:
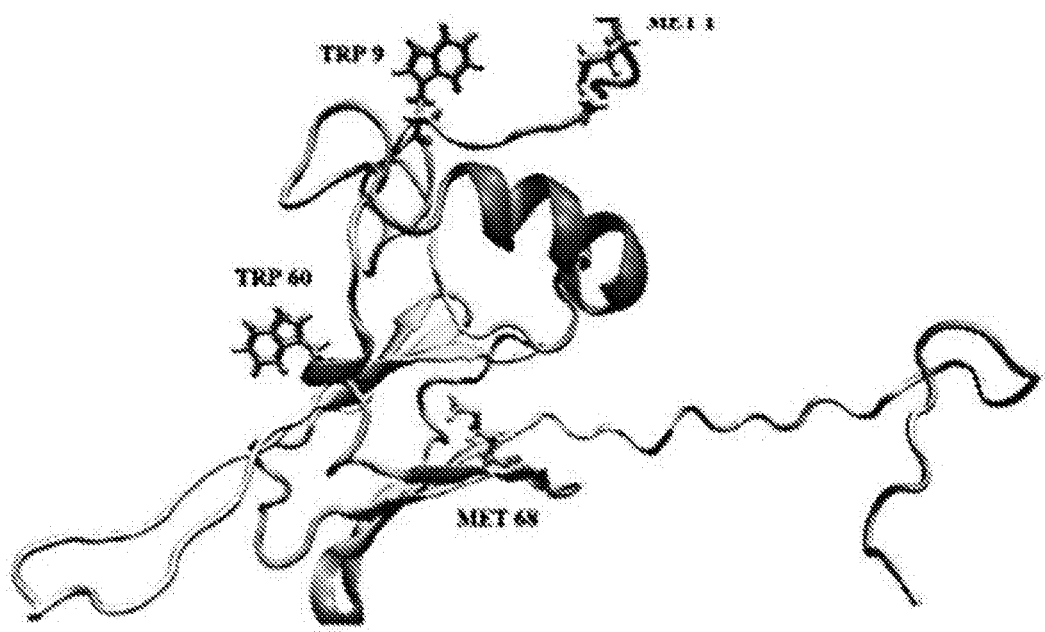

Secondary structure is determined by circular dichroism spectroscopy in the "far-UV" spectral region (190-250 nm). At these wavelengths the chromophore is the peptide bond, and the signal arises when it is located in a regular, folded environment. α-crystallin is mainly made of beta sheets and hence the signal is observed as a downward trough at around 220 nm. With increase in period of glycation, unfolding occurs leading to formation of random coil (FIG. 38).

Tryptophan

Figure 30:
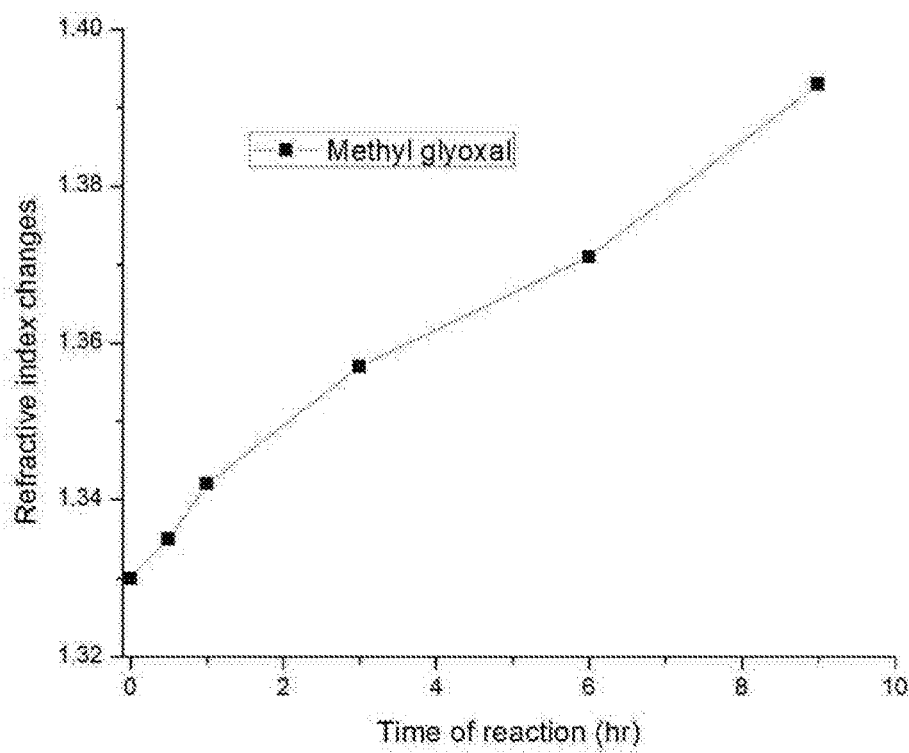
FIG. 30. Change in refractive index due to formation of high molecular weight aggregates and advanced glycation endproducts after glycating α-crystallin using 10 μM methyl glyoxal over a period of 9 hr at 25° C.
Figure 31:
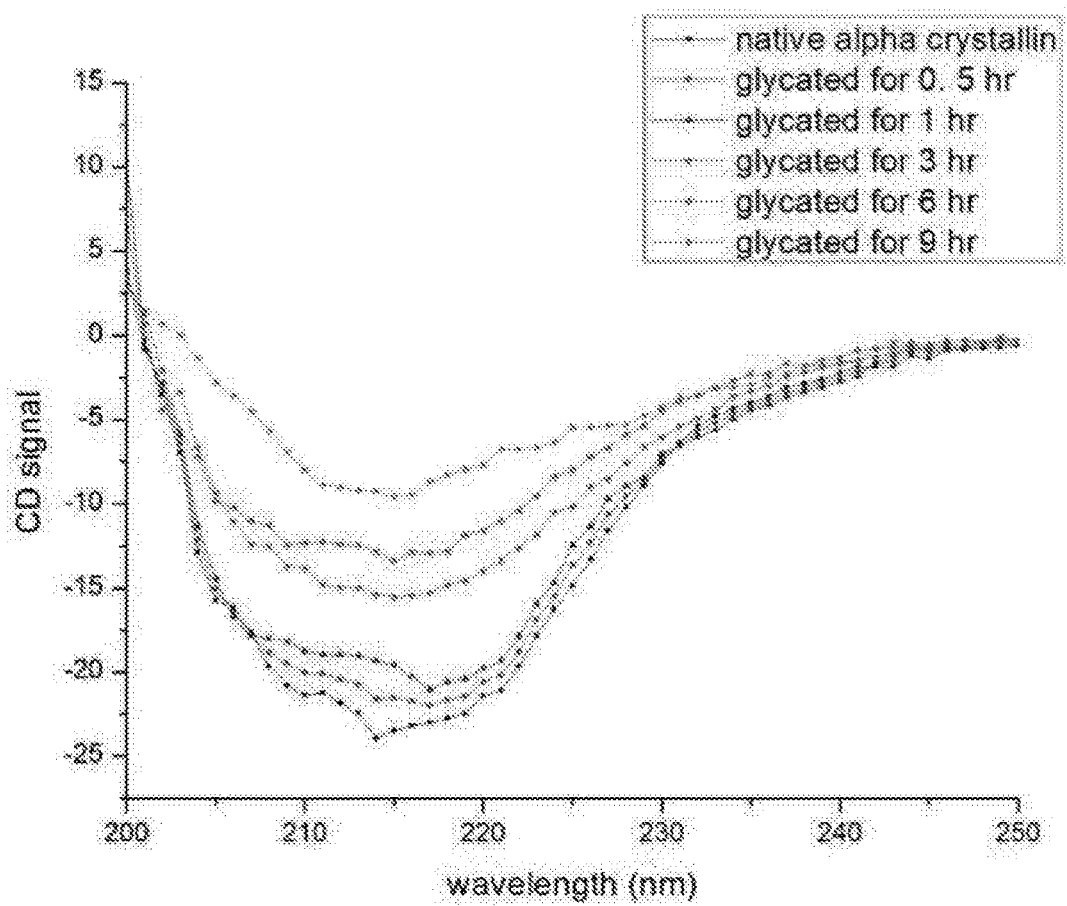
FIG. 31. Change in secondary structure of α-crystallin with increase in time of glycation using 10 μM methyl glyoxal over a period of 9 hr at 25° C.

One of the major fluorophores in proteins is tryptophan. With increase in glycation, tryptophan fluorescence decreases (FIG. 30). But, tryptophans in α-crystallin do not undergo chemical modification due to Maillard reaction as there are no free amino groups. Tryptophan fluorescence is a very valuable tool that can be applied to study folding/unfolding, the effect of environment and solvent exposure on the integrity of the protein. The fluorescence lifetimes of tryptophan can be used to analyze the location of tryptophan and the possibility of short range interactions (Table 5).

Figure 34:
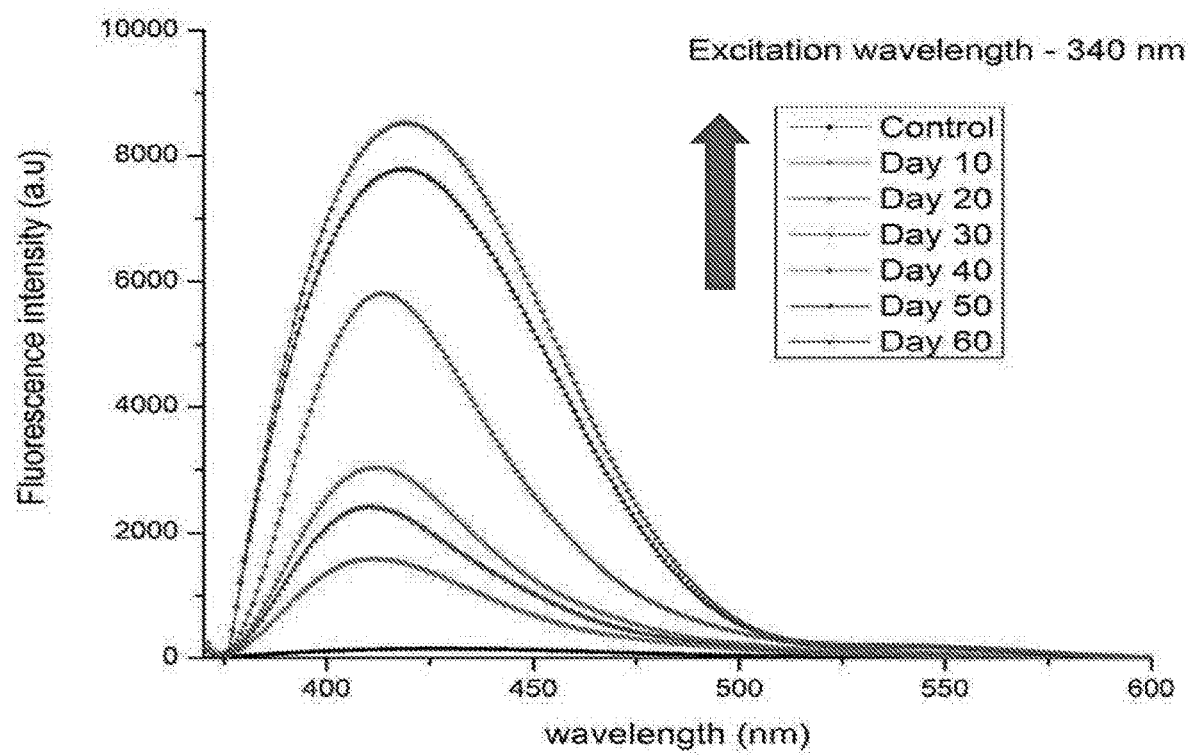
FIG. 34. Steady state fluorescence spectra of α-crystallin with increase in time of glycation at an excitation wavelength of 340 nm.
Figure 35:
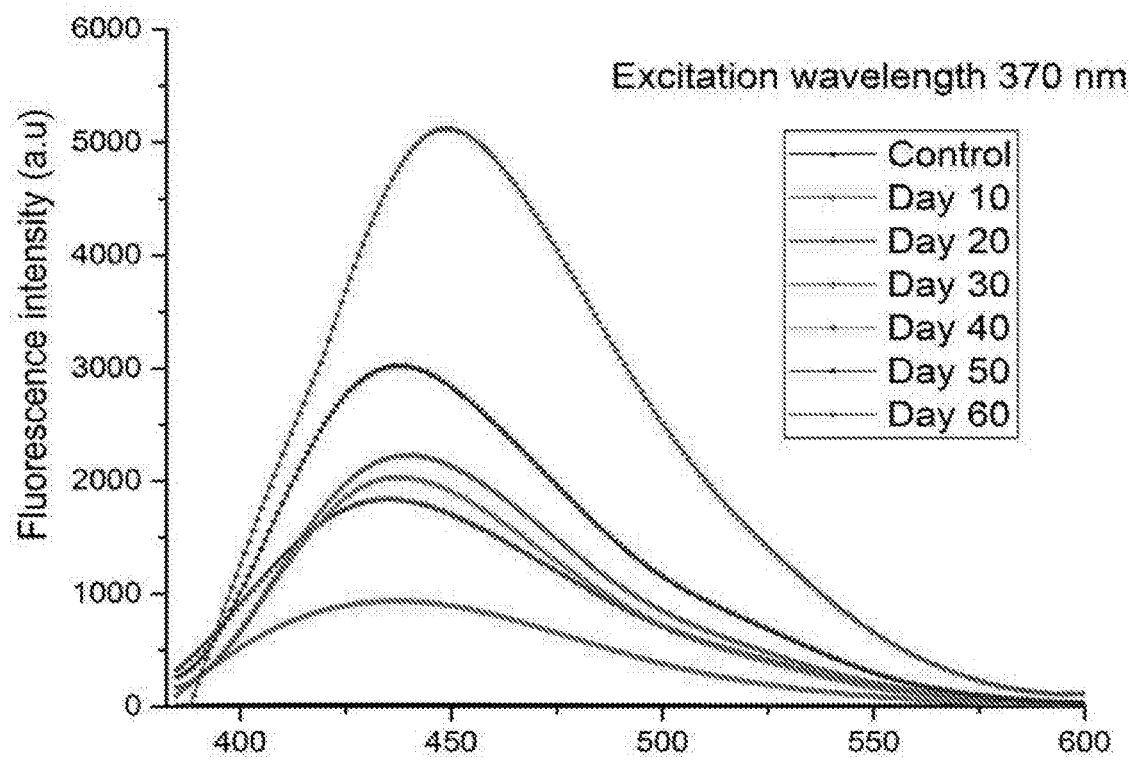
FIG. 35. Steady state fluorescence spectra of α-crystallin with increase in time of glycation at an excitation wavelength of 370 nm.
Figure 36:
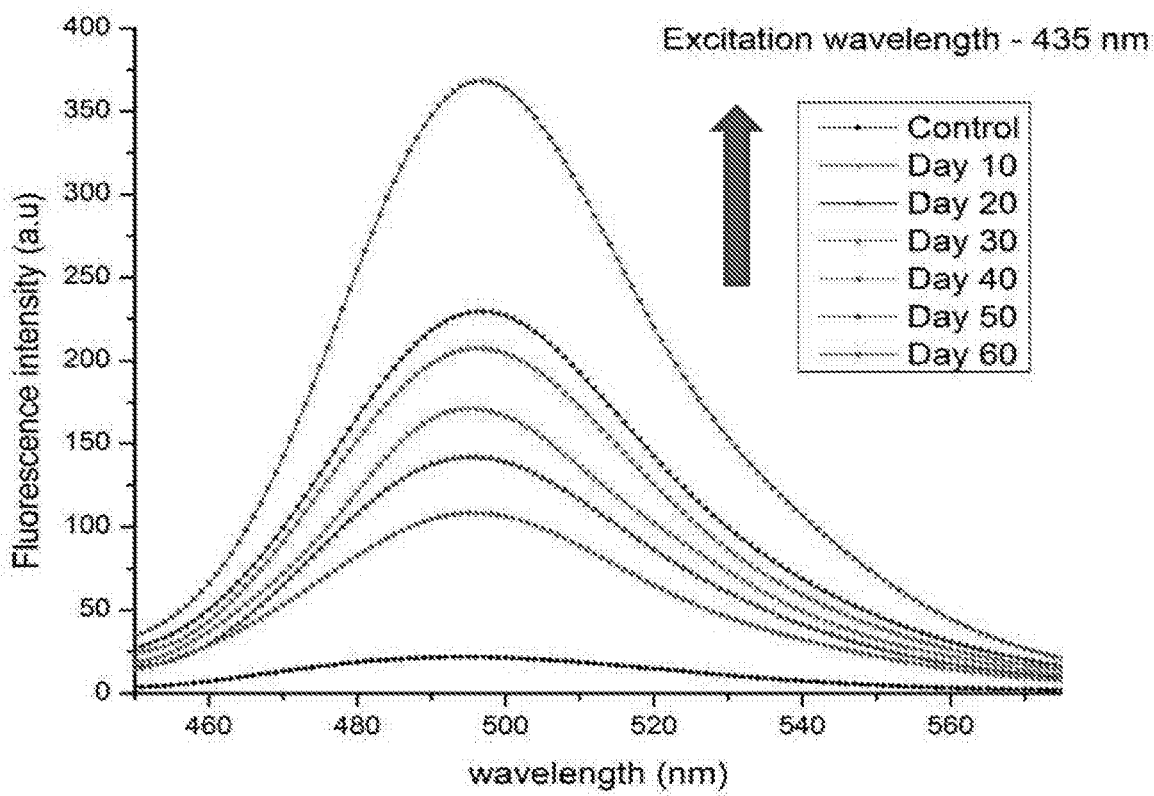
FIG. 36. Steady state fluorescence spectra of alpha crystallin with increase in time of glycation at an excitation wavelength of 435 nm.

FIGS. 10, 11, 12, 33 provide case studies comparing the spectroscopic hotspots in lens autofluorescence for similar aged donor non-diabetic and diabetic lenses. Emission spectra were recorded for the excitation wavelengths set at 340, 370 and 435 nm. By excitation at 340 and 370 nm, emission spectra showed one distinct peak (FIGS. 34 and 35) located at about 440 and 460 nm compatible with the absorption caused by AGEs. A broad band was observed at 500 nm by increasing the excitation wavelength to 435 nm (FIG. 36). Fluorescence emission spectra were also recorded from intact lenses from donors with and without diabetics. Qualitatively, the shape and peak value of the emission spectra excited at the same wavelength were very similar for α-crystallin and the intact lenses (FIGS. 4 and 5), indicating the fluorophore formation in lens crystallins.

Time-resolved fluorescence measurements were analyzed from the fluorescence decay assuming that the model followed a triple exponential fit. In the case of 340 and 370 nm excitation, one or two exponential functions did not provide an acceptable fit, as judged by autocorrelation, number of weighted residuals and Durbin Watson parameters. The lifetimes and their relative contributions were determined at excitation wavelengths—340 and 370 nm as seen in Tables 8 and 9. The overall fluorescence lifetimes were longer for excitation at 370 nm but they did not change with time of glycation in either cases. Table 2 shows the fluorescence lifetimes from unmodified and modified α-crystallin at an excitation wavelength of 435 nm. There are noticeable trends in the lifetimes with glycation of the protein. In the visible region, unmodified α-crystallin showed no fluorescence and therefore, no lifetimes. However, for glycated α-crystallin, new shorter and longer lifetimes were observed with increase in the time of glycation.

Steady state and time resolved fluorescence measurements were collected from intact non-diabetic and diabetic lenses ranging from 6 to 92 year old donors. An illustration of difference in the spectral profiles from donor lenses of 3 different age groups can be seen in FIGS. 4 and 5. Table 3 provides an overall summary of time resolved fluorescence lifetimes obtained at 340 nm from various donor lenses. A sample of time resolved fluorescence data comparisons from non-diabetic and diabetic donor lenses from different age groups can be observed in Tables 10-13. Table 4 provides an overall summary of time resolved fluorescence lifetimes obtained by excitation at 435 nm from various donor lenses. From this data, it can be seen that the distribution of lifetimes and their individual contribution to the total fluorescence at 435 nm excitation wavelength is very different for non-diabetic and diabetic donor lenses. Although the younger non-diabetics did not show any fluorescence, older non-diabetics showed one fluorescence lifetime around 4.7 ns. In the diabetic lenses from younger donors, the time resolved fluorescence decay spectra showed a very good fit with a double exponential decay with lifetimes around 4.6 and 17 ns. The decay spectra from older diabetic donor lenses gave a good fit with triple exponential decay with lifetimes around 1.4, 4.5 and 16 ns.

Amplified concentrations of glycating agents in the body cause modifications in glycoproteins as well as heat shock proteins which is a characteristic feature of aging and diseases like diabetes, cancer and Alzheimer's. AGE formation was evaluated in vitro through incubation of α-crystallin with various glycating agents, for example glucose, sucrose, glycolaldehyde (GA) and methyl glyoxal (MGO). Tryptophan and AGE fluorescence was used to evaluate α-crystallin damage.

Figure 18:
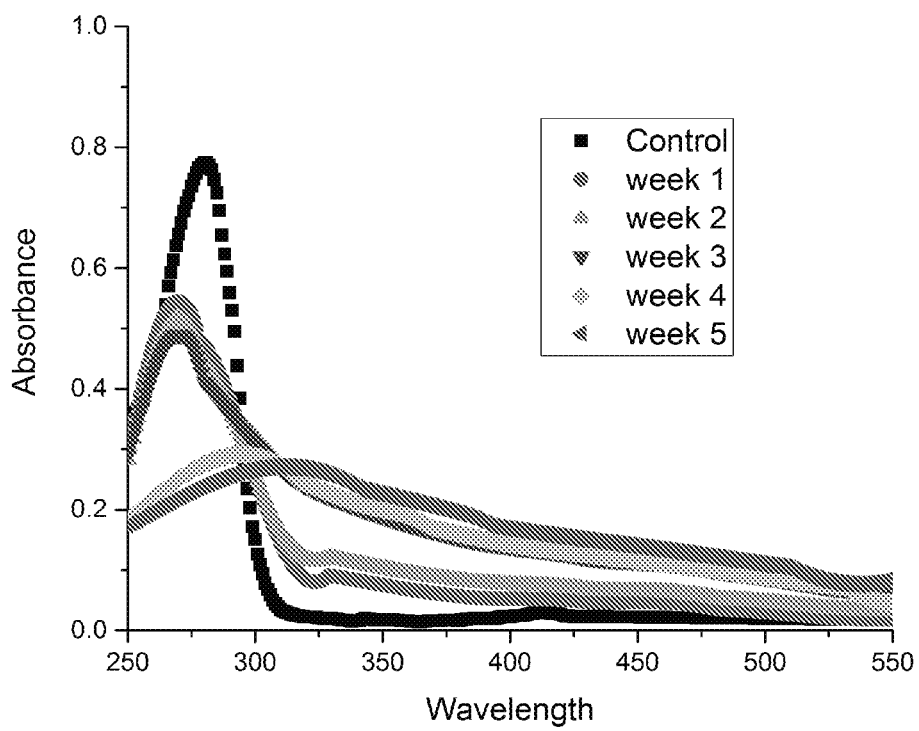
FIG. 18. Change in UV-Vis spectrum of α-crystallin after incubating with 0.05M glycolaldehyde at 25° C. over a period of 5 weeks.
Figure 19:
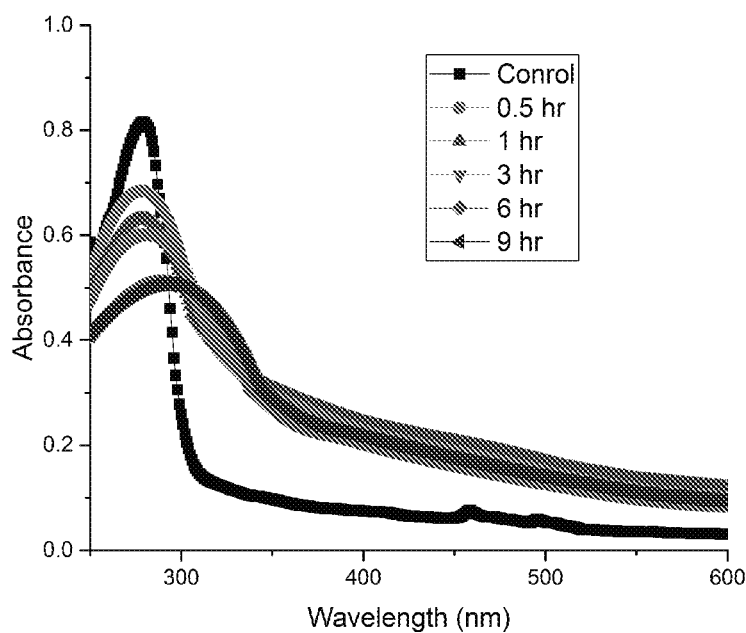
FIG. 19. Change in UV-Vis absorbance of α-crystallin after incubating with 10 μM methyl glyoxal at 25° C. over a period of 9 hr.
Figure 20:
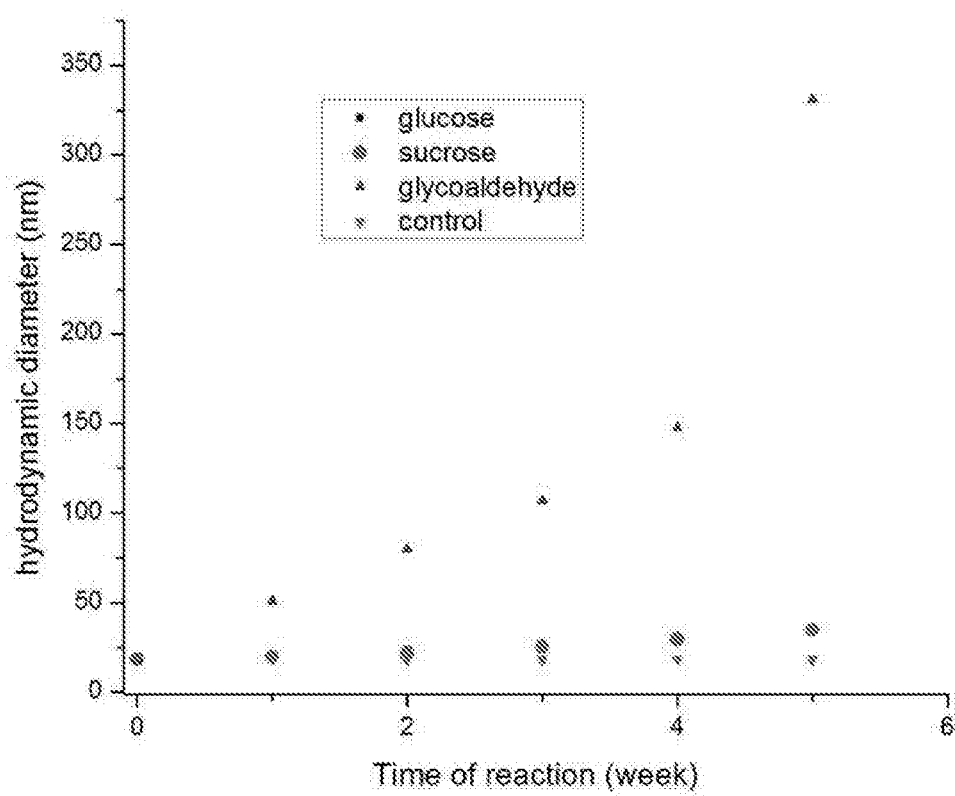
FIG. 20. Change in hydrodynamic diameter of α-crystallin after incubating with 1M glucose, 1M sucrose and 0.05M glycolaldehyde at 25° C. over a period of 5 weeks.
Figure 21:
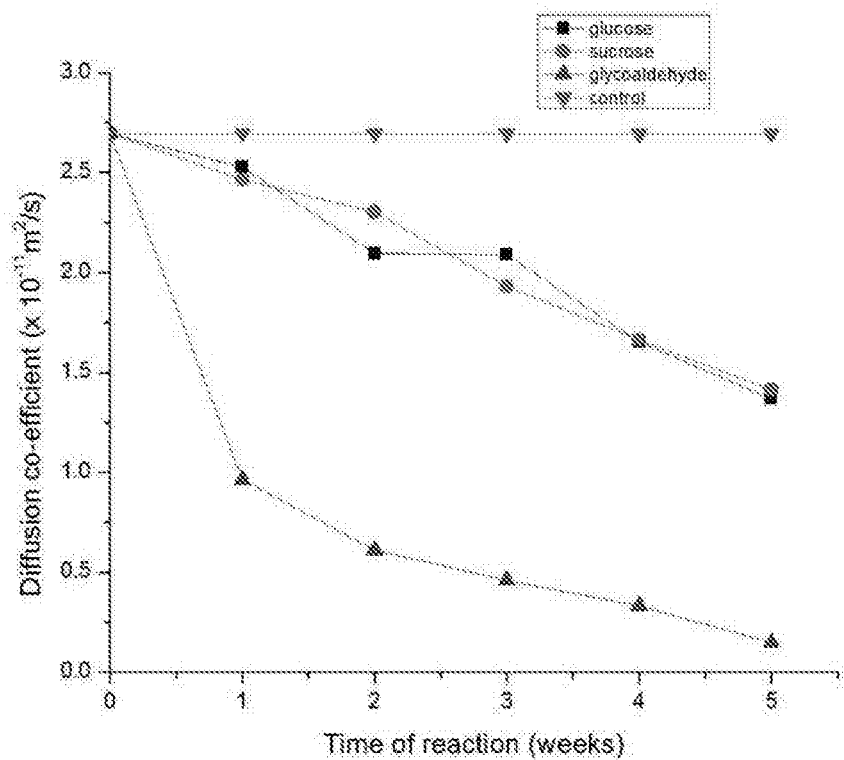
FIG. 21. Change in translational diffusion coefficients of α-crystallin after incubating with 1M glucose, 1M sucrose and 0.05M glycolaldehyde at 25° C. over a period of 5 weeks.
Figure 22:
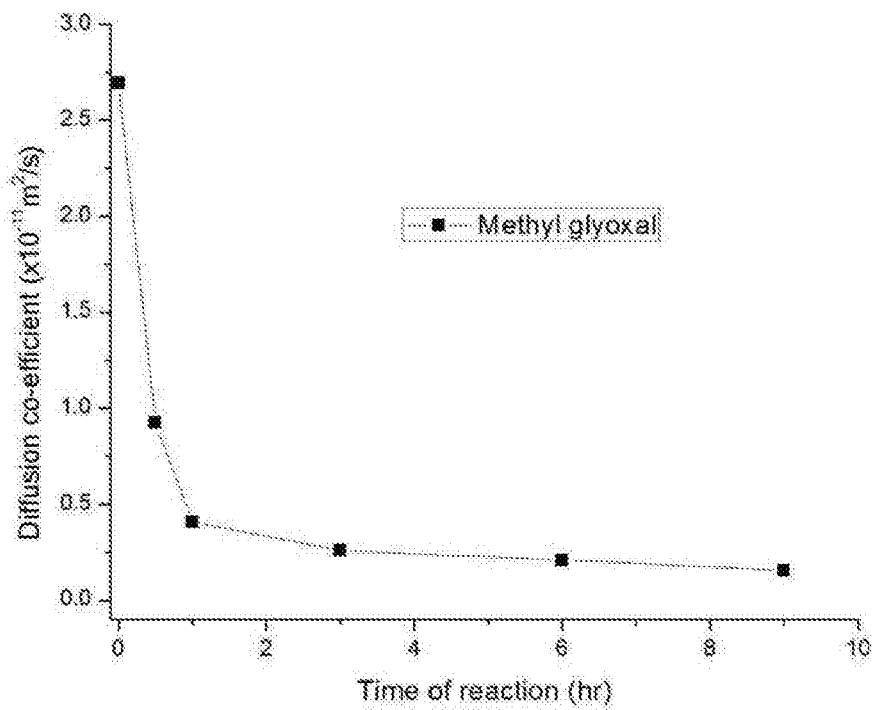
FIG. 22. Change in translational diffusion coefficients (Diffusivity) of α-crystallin after incubating with 10 μM methyl glyoxal at 25° C. over a period of 9 hr.

The protein solutions have shown very good light scattering ability and the particle size of native state α-crystallin was found to be 18±2 nm. When incubated with glucose and sucrose, there was no effect on the particle size of α-crystallin over a period of 5 weeks. With glycolaldehyde, the particle size slowly increased from 18 to 350 nm over a period of 5 weeks when incubated at 25° C. The reaction with MGO was relatively faster and the particle size of the aggregates was around 350 nm within 9 hours (FIG. 6). The change in the absorbance and appearance of new excitation maxima with increase in time of glycation is shown in FIGS. 18 and 19 for GA and MGO respectively. As there was an increase in the particle size, the corresponding diffusivity of the protein decreased. By measuring the light scattering from the lens and in turn particle size of the aggregates, the formation of a cataract is predicted at a very early stage. The calculated diffusivity values from the in vitro study agree with the results obtained from the in vitro study to determine the protein diffusivity in rabbit lenses. By measuring the light scattering from the lens and in turn particle size of the aggregates, the formation of a cataract at a very early stage can be predicted.

Figure 25:
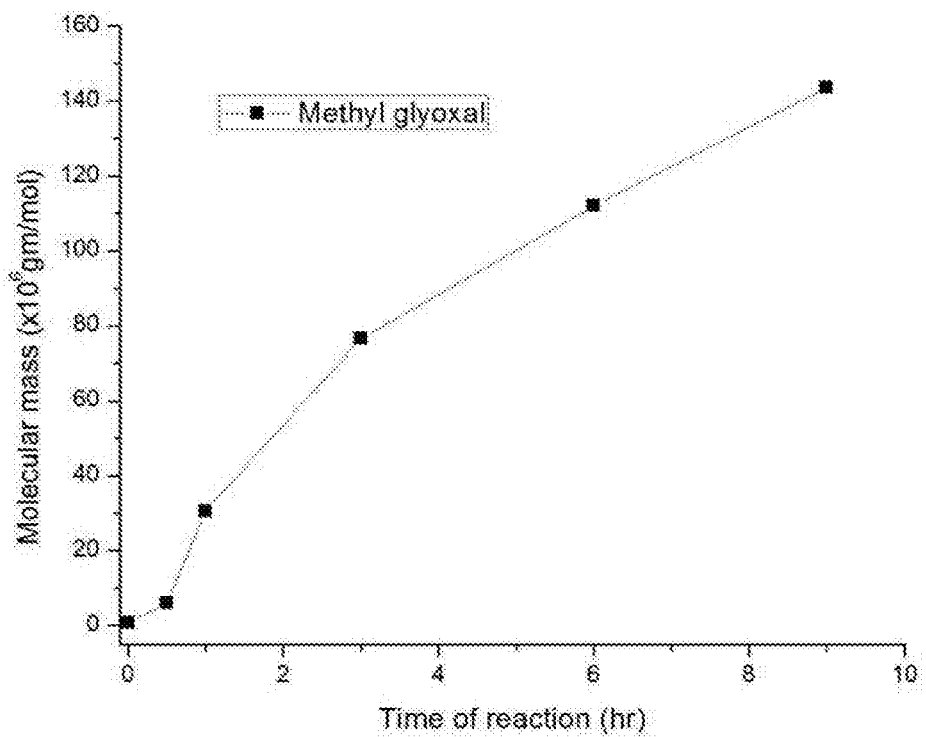
FIG. 25. Static Light Scattering data of 10 μM methyl glyoxal modified α-crystallin at 25° C. showing an increase in molecular mass with time of glycation.

A large increase in the molecular weight of α-crystallin was followed using static light scattering (FIG. 25). A cataract may be a manifestation of high molecular weight protein aggregates. Aggregates may be formed by lens protein cross links linked by disulfide or covalent bonds as monitored by gel electrophoresis and mass spectrometry. These aggregates may be present randomly in the lens and have an ability to diffuse freely leading to increase of light scattering and thereby change in the refractive index of the lens.

Increase in temperature is associated with thermal aggregation as well as increase in the spacing. The effect of glycation on short range interactions and spacing, X-ray scattering profiles of 250 mg/ml α-crystallin glycated with 10 μM methyl glyoxal were studied as shown in FIG. 27. A shift and formation of a weak peak was observed at lower scattering angles with a $Q_{max}$ of 0.025/Å which gives a spacing value of 25.1 nm. The weak scattering peak maxima is likely due to loss of structural integrity of the protein and spherical symmetry of the hetero-oligomeric complex.

Molecular chaperones are a class of proteins which help in the refolding of unfolded proteins to their native state. In the absence of chaperones, these unfolded proteins may mutually associate via exposed hydrophobic regions and precipitate out of solution. Chaperones have an important role in protein folding and refolding by stabilizing the unfolded proteins, hence protecting them from stress conditions. α-crystallin has been shown to function as a molecular chaperone in preventing thermal aggregation of crystallins and other proteins. ANS fluorescence for surface hydrophobicity has been used for the spectroscopic investigation of the high molecular weight complex formed as a result of glycating bovine α-crystallin. The surface hydrophobicity increases with the time of glycation providing more hydrophobic surfaces. The chaperone ability of methyl glyoxal modified α-crystallin increases initially. However, with increased time of glycation, the protein aggregates, loses its structural integrity and chaperone ability. As a result, other lens proteins are easily prone to stress leading to their damage. Structural results disclosed herein explain the loss of chaperone activity reported by others, thereby establishing the relation between structure and function of alpha crystallin.

Figure 29:
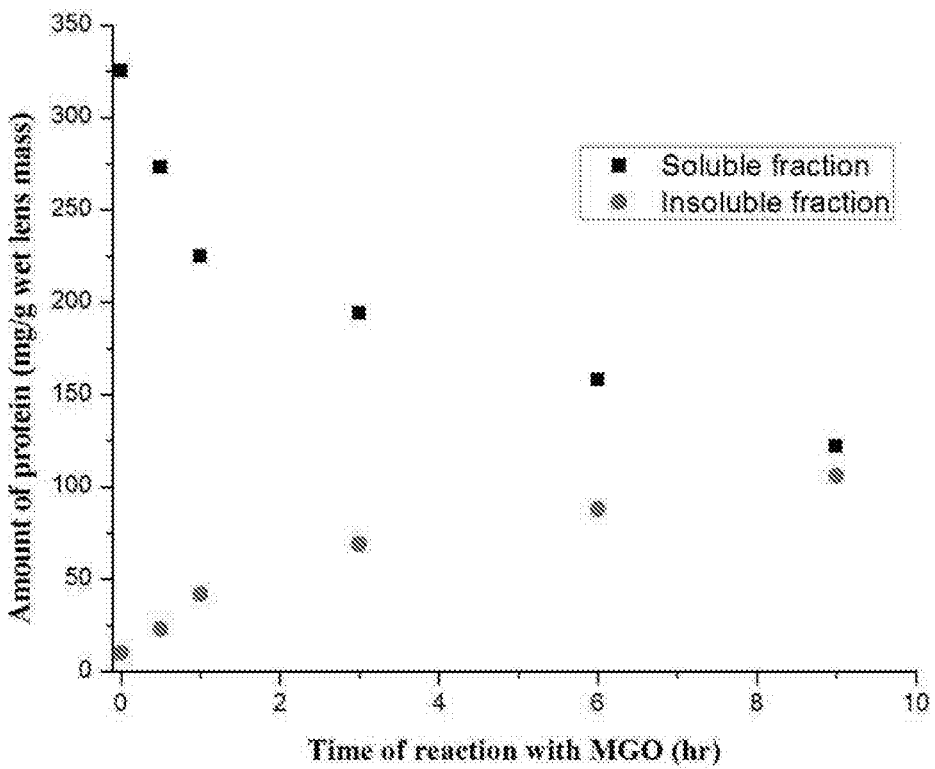
FIG. 29. Changes in the amount of water soluble and insoluble fractions from the control calf lens (0 hr) and 10 μM methyl glyoxal modified calf lens over a period of 9 hr at 25° C.

The formation of aggregates, change in inter-particle spacing and decreased protein diffusivity also affect the physicochemical parameters of the proteins. The intricate complexation and arrangement of α-crystallin is responsible for the transparency of the lens. FIG. 29 shows that the soluble portion of the protein decreases drastically over time. At the same time, the refractive index of native α-crystallin which has to be close to that of water also changes as shown in FIG. 30. Change in refractive index leads to increased light scattering in the eye and may be the reason for chromatic aberration that occurs with cataracts and in presbyopia. Overall, the formation of high molecular weight aggregates due to glycation leads to a change in both the scattering intensities as well as the spectroscopic properties of the lens.

Figure 32:
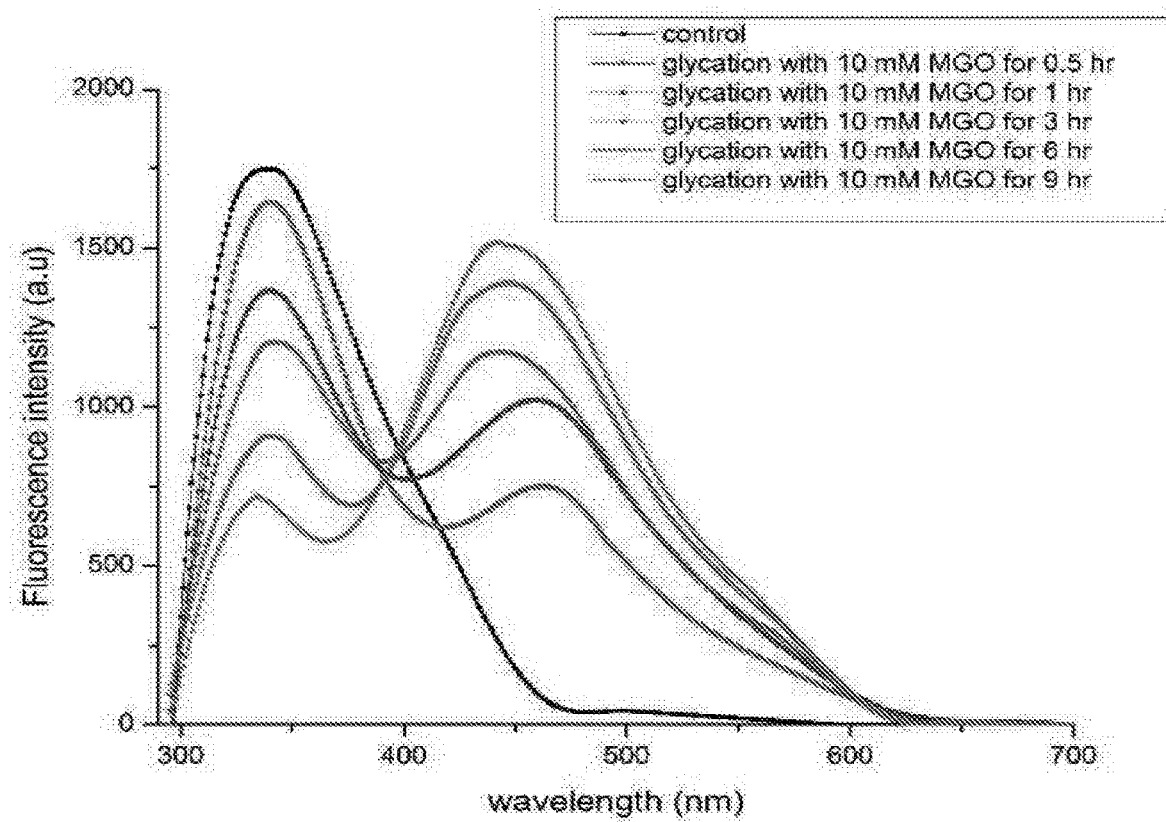
FIG. 32. Change in tryptophan fluorescence of α-crystallin after incubating with 10 μM methyl glyoxal over a period of 9 hr at 25° C.
Figure 33A:
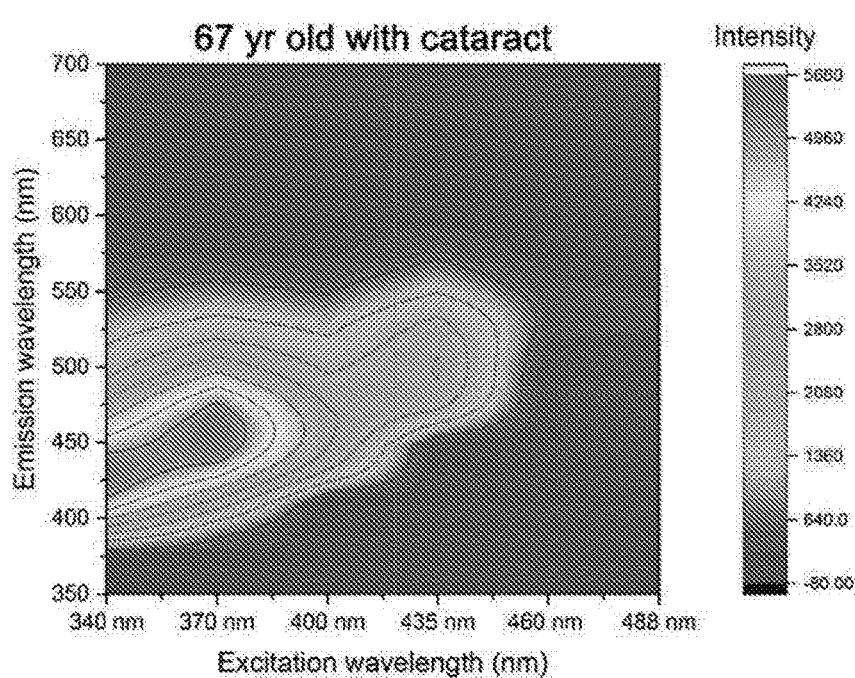
FIG. 33. Comparison of steady state fluorescence hotspots between FIG. 33B. 64 yr old non-diabetic and FIG. 33A. 67 yr old with cataracts.
Figure 33B:
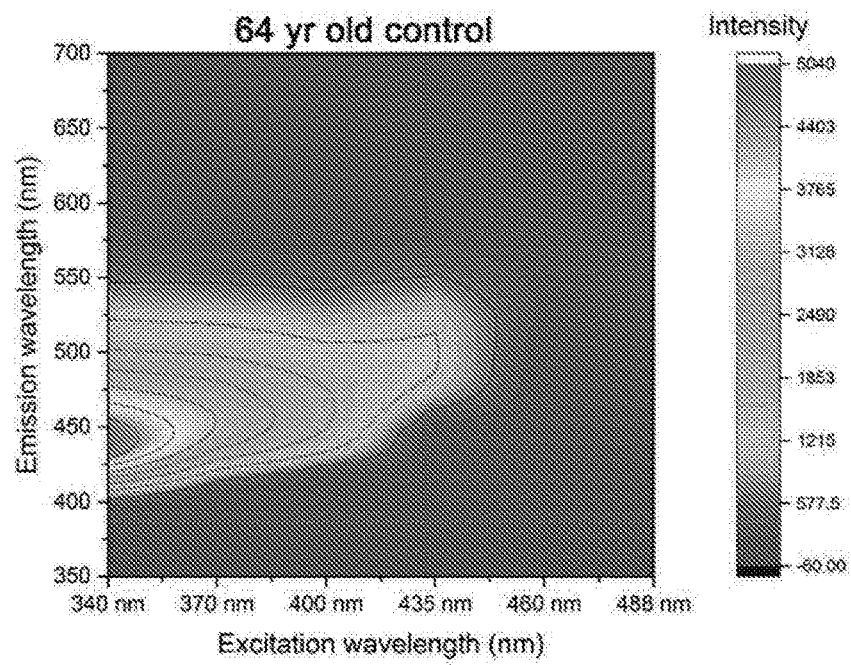

Far UV circular dichroism (CD) spectra reflect the changes in secondary structure of the proteins. Both the native state and glycated α-crystallin showed a minimum at 217 nm which indicates beta sheets (FIG. 32). However, with the progression of glycation, α-crystallin showed a considerable decrease in the negative ellipticity and a tendency to shift towards the left. Loss of structural stability due to the formation of random coils can be concluded from the CD data. This can be explained by the formation of high molecular weight aggregates and increase in surface hydrophobicity. Presence of these residues in the random coil may explain the increase in hydrophobicity of the protein associated with the loss of beta sheets.

Tryptophan has a very strong fluorescence in the proteins. The residues which are buried in the hydrophobic core of proteins can have spectra which are shifted by 10 to 20 nm compared to tryptophans on the surface of the protein. Tryptophan fluorescence is quenched due to microenvironments. In case of α-crystallin, the unmodified protein seems to have more fluorescence than the modified as shown in FIG. 32. The magnitude of fluorescence intensity can serve as a probe to explain the perturbations occurring in the native state. The wavelength maxima of tryptophan fluorescence shifted on modification indicating a change in the microenvironment which can be confirmed by surface hydrophobicity measurements (FIG. 28). In α-crystallin, tryptophans are not located at the N-terminus and hence do not have a free amino group to participate in the Maillard reaction. The photo degradation products of alpha crystallin are primarily from tryptophan oxidation.

There is a shift in the isosbestic point of the spectra. Usually, the presence of an isosbestic point indicates that only two species that vary in concentration contribute to the absorption around the isosbestic point. If a third molecule is participating in the process, the spectra typically intersect at varying wavelengths as concentrations change, creating the impression that the isosbestic point is 'out of focus', or that it will shift as conditions change. The reason for this is that the different compounds have varying extinction coefficients at one particular wavelength. Tryptophan oxidation products have spectral profiles similar to AGEs with varying extinction coefficients. Tryptophan fluorescence decreased with increase in the time of glycation.

Advanced glycation end-products have a characteristic fluorescence and are excited in the spectral region of tryptophan emission. Generation of AGEs can be associated with oxidative stress, tobacco smoking and weakened detoxification of AGE precursors. Compared to sugars like glucose and sucrose, the dicarbonyl intermediates cause a lot of damage. This indicates that the rate of AGE formation also depends on the rate of breakdown of sugars into the highly reactive intermediates which in turn is dependent on many intrinsic and extrinsic factors. The change in AGE fluorescence with decrease in tryptophan fluorescence can be observed in FIG. 30 and FIG. 32.

Tryptophan (Trp) lifetime measurements is used to give a rough idea about the changes in the microenvironments. Tryptophan fluorescence is a very valuable tool that can be applied to study folding/unfolding, the effect of environment and solvent exposure on the integrity of the protein. The fluorescence lifetimes of tryptophan can be used to analyze the location of tryptophan and the possibility of short range interactions. Fluorescence of α-crystallin is predominantly due to the Trp 9 in both A and B chains while the Trp 60 present in the B chain is buried from exposure. However, after the process of glycation begins, the tryptophans are completely exposed to the surrounding aqueous medium. This can be confirmed from the lifetime measurements as in Table 5, no change was observed in the lifetimes with time of glycation. However, the measurements hint at a possibility that the tryptophan residues undergo a shift in their position once the protein starts to unfold and aggregate leading to the formation of water insoluble residues.

Predicted flow velocity is extremely slow considering the nutrients transported increase the viscosity of the fluid. This is in tune with the very low diffusion coefficient data obtained from dynamic light scattering data. Glucose and sucrose pass through the lens but do not spontaneously react with the proteins. On the other hand, glycolytic intermediates like methyl glyoxal are extremely reactive and start forming Schiff's bases when they come in contact with the protein and instantaneously lead to the formation of AGEs. Also, the aggregates cause an irreparable damage to the intricate protein network causing opacification which is most commonly observed in case of cataracts.

Non enzymatic glycation of the proteins is a characteristic feature of aging and diseases like diabetes.

The main contributing fluorophore when excited in the UV region is reported to be argpyrimidine. The effect of different microenvironments on the emission spectrum and fluorescence lifetimes explains the red shift. However, the fluorescence lifetimes did not change with time of glycation. This shows that the fluorescence lifetimes measured in this region are not affected by glycation.

MATERIALS AND METHODS

Methyl glyoxal was purchased from Sigma Aldrich. Fresh bovine lenses were obtained from the Aurora meat packing company, Illinois. Whole human donor lenses were obtained from the Eye Bank within 2 days after death. The lenses from donor age range of 40-90 years were used for this study. The lenses were stored at $-70°$ C. in the dark till the day of use.

A) Extraction of Bovine Alpha Crystalline:

Fresh bovine lenses were weighed and then homogenized by stirring in a buffer prepared using 50 mM Tris/0.2 M NaCl/1 mM EDTA/10 mM mercaptoethanol, pH 7.4 at 4° C. The supernatant was centrifuged at 14000 g for 1 hr. at 4° C. Alpha-crystallin was isolated from the total soluble lens protein solution by size exclusion chromatography. A total of 30 ml supernatant was loaded on a 1.7 cm×100 cm CL-6B sepharose gel filtration column, and using a peristaltic pump, eluted at a flow rate of 1 ml/min and monitored by absorbance at 280 nm. Alpha crystallin elutes first as a single symmetrical peak at approximately 170 ml of the buffer corresponding to an apparent molecular mass of 800 KDa. The isolated α crystallin fractions were pooled and desalted with Ultrafree-15 Biomax-10K centrifugal filter devices (Millipore Corporation, Bedford, Mass.) at a speed of 3000 rpm by rinsing three times with water. The purity of the sample was determined by SDS-PAGE with the Pharmacia LKB*Phast System and by mass spectrometry (45).

B) Sample Preparation:

Bovine alpha crystallin was used as the model protein to study the progression of glycation. Methyl glyoxal (MGO) was used as the glycating agent at a concentration of 2.5 μM in 1 mg/ml alpha crystallin solution and incubated at 25° C. over a period of 60 days. The aliquots were collected at regular intervals and dialyzed against 10 mM phosphate buffer, pH 7.4.

C) Steady State Fluorescence Measurements:

The AGE fluorescence of unmodified and methyl glyoxal modified alpha-crystallin was measured using Hitachi F2500 Fluorescence Spectrometer. The fluorescence emission spectrum of the samples was recorded using 340 and 435 nm as excitation wavelength maintaining the slit widths at 5 nm and PMT voltage of 400V. The same procedure was repeated using the whole donor lenses to study the spectral properties of the fluorophores.

D) Time Resolved Fluorescence Measurements:

The lifetime profiles for the fluorescence decay of fluorophores in unmodified and modified alpha crystallin (10 mM phosphate buffer at pH 7.4) were measured in triplicate by using TimeMaster™ LED system (TM-2000). The samples were excited in UV-A region at 340 nm and in visible region at 435 nm using a LED light source having approximately 1.5 ns pulse width. The time domain system was used to measure the decay in fluorescence with respect to time. The raw decay data was analyzed using global 1 to 4 three exponential fitting analysis with deconvolution which gives the lifetimes as well as the relative contributions to the total fluorescence at time zero. These data were assessed with a good auto correlation function around zero, weighted number of residuals randomly distributed between +3 and −3, reduced $\chi^2$ values between 0.9 to 1.1 and the Durbin-Watson parameters of greater than or equal to 1.6, 1.7 and 1.8 for one, two and three exponential decay respectively. Once the lifetimes were obtained using the model protein, the procedure was extended to measure the fluorescence lifetimes of the intact lenses of diabetic and non-diabetic donors. The donor lenses were positioned parallel to excitation source and the emission was detected at right angles to the excitation beam.

Methyl glyoxal was purchased from Sigma Aldrich. Fresh calf lenses were obtained from the Brown Packing Co. (South Holland, Ill.).

E) Extraction of Bovine Alpha Crystallin:

Fresh calf lenses were weighed and then homogenized by stirring in a buffer prepared using 50 mM Tris/0.2 M NaCl/1 mM EDTA/10 mM mercaptoethanol, pH 7.4 at 4° C. The supernatant was centrifuged at 14000 g for 1 hr at 4° C. α-crystallin was isolated from the total soluble lens protein solution by size exclusion chromatography. A total of 30 ml supernatant was loaded on a 1.7 cm×100 cm CL-6B sepharose gel filtration column, and using a peristaltic pump, eluted at a flow rate of 1 ml/min and monitored by absorbance at 280 nm. Alpha crystallin elutes first as a single symmetrical peak at approximately 170 ml of the buffer corresponding to an apparent molecular mass of 800 KDa. The isolated α crystallin fractions were pooled and desalted with Ultrafree-15 Biomax-10K centrifugal filter devices (Millipore Corporation, Bedford, Mass.) at a speed of 3000 rpm by rinsing three times with water. The purity of the sample was determined by SDS-PAGE with the Pharmacia LKB*Phast System and by mass spectrometry.

F) Sample Preparation:

Bovine α-crystallin was used as the model protein to study the progression of glycation. Methyl glyoxal (MGO) was used as the glycating agent at a concentration of 10 μM in 1 mg/ml alpha crystallin solution and incubated at 37° C. over a period of 9 hours. The aliquots were collected at 0.5, 1, 3, 6, 9 hr. The samples were dialyzed against 10 mM phosphate buffer, pH 7.4, lyophilized and reconstituted with 1 ml of MQ water before measurements.

G) Dynamic Light Scattering Measurements (DLS)

Particle sizes, and particle cluster sizes were measured using DLS on a Brookhaven BI-200SM Research Goniometer and Laser Light Scattering System. For a spherical particle diffusing through a solution of viscosity η the intensity correlation function ($g_2$) measured through DLS decays with an exponential relaxation rate, $g_2(t)=1+\beta\exp(-2\Gamma t)$. The particle size can be obtained from the decay rate via $R=k_B Tq^2/6\pi\eta\Gamma$. Here $k_B$ is Boltzmann's constant, T is the temperature and $$q = 4\pi\sin\left(\frac{\theta}{2}\right)/\lambda$$

is the scattering vector of the laser light scattered at θ=90° and λ=632 nm.

For a suspension consisting of a mixture of particles of varying size the distribution of sizes can be obtained from an inverse Laplace transform. We used the CONTIN software package to obtain particle size distributions in this manner. The accuracy of the distributions was determined based on the polydispersity and the baseline difference from the correlation curve.

H) Surface Hydrophobicity Measurements

The surface hydrophobicity of the native and MGO modified alpha crystallin was studied using a specific hydrophobic probe, 1-anilinonaphthalene-8-sulfonic acid (ANS). Ten microliters of a 10 mM methanolic solution of ANS was added to 1 mL of protein [0.1 mg/mL in 10 mM phosphate buffer (pH 7.4)], and the mixture was incubated for 1 hr in the dark at 25° C. Fluorescence emission spectra were recorded between 400 and 600 nm using an excitation wavelength of 370 nm. The excitation and emission bandpasses were 5 nm each.

I) Small Angle X-Ray Scattering Measurements

Concentrated samples of alpha crystallin and glycated alpha crystallin have been studied using SAXS. These studies were performed at the 8-ID-I beam line of the Advanced Photon Source at Argonne National labs, IL. The sample in a sealed capillary was placed in the beam line under vacuum. Coherent X ray photons of energy 7.35 keV were focused using a Kinoform lens placed upstream of the sample. The scattered photons were detected by a PI LCX-1300 direct detection CCD (Princeton Instruments, USA) 4.0 m downstream of the sample. A single camera width spans about 0.3 nm$^{-1}$ in the scattering vector (Q) space. The intensities were measured at 6 overlapping camera widths covering a Q range from 0.1-1 nm$^{-1}$. For a given camera position, 20 frames were collected with an exposure time of 0.2 s for each frame. The shorter exposures of 0.2 s and moving the beam spot to a different location and camera to a new position helps to minimize the radiation damage caused by the X-ray beam. The resulting image pixels were analyzed by a MATLAB GUI to obtain the time averaged intensity profiles as a function of the scattering vector. The inter-particle distance between the sub-units can be determined from scattering vector Q using $Q_{max}=2\pi/d$; where, d=distance between adjacent sub-units.

J) Steady State Fluorescence Measurements:

The tryptophan fluorescence of unmodified and methyl glyoxal modified α-crystallin was measured using Hitachi F2500 Fluorescence Spectrometer. The fluorescence emission spectrum of the samples was recorded between 300-700 nm using 295 nm as excitation wavelengths maintaining the slit widths at 2.5 nm and PMT voltage of 400V.

K) Time Resolved Fluorescence Measurements

The lifetime profiles for the tryptophan fluorescence decay in unmodified and modified alpha crystallin (10 mM phosphate buffer at pH 7.4) were measured by using Time-Master™ LED system (TM-2000). The samples were excited at 295 nm using a LED light source having approximately 1.5 ns pulse width. The time domain system was used to measure the decay in fluorescence with respect to time. The raw decay data was analyzed using global 1 to 4 three exponential fitting analysis with deconvolution which gives the lifetimes as well as the relative contributions to the total fluorescence at time zero. These data were assessed with a good auto correlation function around zero, weighted number of residuals randomly distributed between +3 and −3, reduced $X^2$ values around 0.9 to 1.1.

TABLE 1

Time resolved fluorescence lifetimes from glycated α-crystallin by excitation at 340 nm and emission maxima between 420-440 nm.

| Time of glycation with MGO (days) | Lifetimes, $\tau$ (ns) and relative contributions at time zero, A (%) | | | | | | $X^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Control | 70.5 ± 1.5 | 0.5 ± 0.04 | 18.9 ± 1.9 | 2.4 ± 0.02 | 10.6 ± 3.2 | 7.2 ± 0.17 | 0.96 | 1.83 |
| 10 | 65.5 ± 1.4 | 0.6 ± 0.15 | 22.1 ± 1.2 | 2.2 ± 0.3 | 12.4 ± 0.8 | 7.2 ± 0.5 | 1.04 | 1.87 |
| 20 | 54.8 ± 2.9 | 0.6 ± 0.01 | 29.5 ± 1.7 | 2.5 ± 0.07 | 15.7 ± 1.2 | 7.6 ± 0.02 | 0.98 | 1.8 |
| 30 | 49.8 ± 2.9 | 0.7 ± 0.08 | 34 ± 2.7 | 2.8 ± 0.3 | 16.2 ± 2.8 | 7.9 ± 0.32 | 1.031 | 1.92 |
| 40 | 45.3 ± 0.1 | 0.5 ± 0.1 | 37.7 ± 2.1 | 2.3 ± 0.2 | 17 ± 0.95 | 7.9 ± 0.1 | 1.002 | 1.94 |
| 50 | 34.9 ± 1.1 | 0.7 ± 0.1 | 45.2 ± 1.2 | 2.4 ± 0.3 | 19.9 ± 0.7 | 7.85 ± 0.5 | 0.954 | 1.81 |
| 60 | 28.8 ± 4.5 | 0.76± | 50.1 ± 3.2 | 2.78 ± 0.4 | 21.1 ± 1.7 | 8 ± 0.6 | 0.97 | 2.01 |

TABLE 2

Time resolved fluorescence lifetimes from glycated α-crystallin by excitation at 435 nm and emission maxima between 500-510 nm.

| Time of glycation with MGO (days) | Lifetimes, $\tau$ (ns) and relative contributions at time zero, A (%) | | | | | | $X^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Control | — | — | — | — | — | — | — | — |
| 10 | — | — | 100 | 4.7 ± 0.04 | — | — | 0.999 | 1.635 |
| 20 | — | — | 96.11 ± 1.6 | 4.76 ± 0.2 | 3.89 ± 0.06 | 19.5 ± 1.7 | 0.985 | 1.75 |
| 30 | 44.1 ± 0.3 | 1.67 ± 0.1 | 20.1 ± 0.2 | 4.51 ± 0.09 | 35.8 ± 0.6 | 17.6 ± 0.5 | 1.07 | 1.81 |
| 40 | 45.1 ± 0.2 | 1.6 ± 0.11 | 19.7 ± 0.31 | 4.6 ± 0.04 | 35.2 ± 0.01 | 17 ± 0.6 | 1.075 | 1.871 |
| 50 | 58.2 ± 0.2 | 1.4 ± 0.43 | 30.1 ± 0.3 | 4.6 ± 0.14 | 11.8 ± 2.7 | 16.7 ± 0.3 | 1.03 | 1.85 |
| 60 | 51.6 ± 0.2 | 1.5 ± 0.31 | 42.3 ± 0.64 | 4.4 ± 0.43 | 6.07 ± 0.3 | 15.6 ± 1.4 | 0.987 | 1.961 |

TABLE 3

Summary for time resolved fluorescence lifetimes from human donor lenses by excitation at 340 nm and emission maxima between 420-440 nm.

| Type of donor lens | Lifetimes, $\tau$ (ns) and relative contributions at time zero, A (%) | | | | | | $X^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Non-diabetic (n = 35) | 52-65% | 0.62 ± 0.1 | 20-33% | 2.6 ± 0.14 | 13-21% | 7.6 ± 0.2 | 1.04 | 1.97 |
| Diabetic (n = 9) | 38-49% | 0.66 ± 0.1 | 37-45% | 2.3 ± 0.1 | 12-19% | 7.6 ± 0.12 | 1.01 | 1.9 |

TABLE 4

Summary for time resolved fluorescence lifetimes from human donor lenses by excitation at 435 nm and emission maxima between 500-510 nm.

| Type of donor lens | Lifetimes, $\tau$ (ns) and relative contributions at time zero, A (%) | | | | | | $\chi^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Nondiabetic *(<45 year) (n = 10) | — | — | — | — | — | — | — | — |
| Nondiabetic (>45 year) (n = 34) | — | — | 100 | 4.76 ± 0.02 | — | — | 0.967 | 2.14 |
| Nondiabetic (>45 year) (n = 4) | — | — | 58.1 ± 0.5 | 4.6 ± 0.14 | 41.9 ± 0.2 | 16.2 ± 0.05 | 0.992 | 1.76 |
| Diabetic (>45 year) (n = 5) | 37.1 ± 4.8 | 1.6 ± 0.07 | 33.9 ± 5.2 | 4.3 ± 0.02 | 29 ± 2.6 | 15.1 ± 0.01 | 0.985 | 2.06 |

*No disease conditions and ocular history.

TABLE 5

Changes in tryptophan lifetimes of α-crystallin after incubating with using 10 μM methylglyoxal over a period of 9 h at 25° C.

| Time of glycation with methyl glyoxal (h) | Lifetimes, $\tau$ (ns) and relative contributions at time zero, A (%) | | | | | | $\chi^2$ value |
|---|---|---|---|---|---|---|---|
| | $A_1$ | $\tau_1$ | $A_2$ | $\tau_2$ | $A_3$ | $\tau_3$ | |
| 0 | 16.1 | 1.3 | 53.4 | 4.3 | 30.5 | 9.6 | 0.97 |
| 0.5 | 12.3 | 1.5 | 48.5 | 4 | 39.2 | 9.8 | 1.11 |
| 1 | 14.7 | 1.5 | 44.4 | 5 | 40.9 | 9.8 | 1.08 |
| 3 | 16.1 | 1.7 | 42.3 | 4.9 | 39.5 | 9.8 | 1.21 |
| 6 | 17.4 | 1.8 | 48.2 | 4.9 | 34.4 | 10 | 1.01 |
| 9 | 18.2 | 2.3 | 43.7 | 3.5 | 40.2 | 10 | 0.99 |

TABLE 6

Sequences

MDIAIHHPWIRRPFFPFHSPSRLFDQFFGEHLLESDLFPTSTSLSPFYLR
PPSFLRAPSWFDTGLS[EMRLEK<u>DRFSVNLDVICHFSPEELKVK</u>VLGDVI
EVHGKHEERQDEHGFISREFHRKYRIPADVDPLTITSSLSSDGVLTVNGP
RKQVSGPERTIPI]TREEKPAVTAAPKK

Black bold-αA-crystallin recognition sites on αB-crystallin
Underline-chaperone site
Bracketed-α-crystallin domain (Sreelakshmi, Santhoshkumar, Bhattacharyya, & Sharma, 2004)

TABLE 7

Criteria for the diagnosis of diabetes and of increased risk for diabetes [pre-diabetes]/Impaired Fasting Glucose [IFG] adopted from ADA-Clinical Practice Recommendations [Diabetes Care, 36 [S1], 2013

| Diabetes Test* | ADA Goal for | |
|---|---|---|
| | Diagnosis of Diabetes | Increased risk [Prediabetes]/IFG |
| HbA1c | | |
| Using a method certified by NGSP and standardized to the DCCT assay. or Fasting Plasma Glucose | ≥6.5% | 5.7-6.4% |
| Fasting is defined as no caloric intake for at least 8 hours. or 2 Hour Plasma Glucose [OGTT] | ≥126 mg/dL (7.0 mmol/L) | 100-125 mg/dL (6.9 mmol/L) |
| The test should be performed as described by the WHO, using a glucose load containing the equivalent of 75 g anhydrous glucose dissolved in water. | ≥200 mg/dL (11.1 mmol/L) | 140-199 mg/dL (7.8-11.0 mmol/L) |

TABLE 8

Time resolved fluorescence lifetimes from glycated alpha crystallin by excitation at 340 nm and emission maxima between 420-440 nm

| Time of glycation with MGO (days) | Lifetimes, $\tau$ (ns) and Relative contributions at time zero, A (%) | | | | | | $\chi^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Control | 70.5 ± 1.5 | 0.5 ± 0.04 | 18.9 ± 1.9 | 2.4 ± 0.02 | 10.6 ± 3.2 | 7.2 ± 0.17 | 0.96 | 1.83 |
| 10 | 65.5 ± 1.4 | 0.6 ± 0.15 | 22.1 ± 1.2 | 2.2 ± 0.3 | 12.4 ± 0.8 | 7.2 ± 0.5 | 1.04 | 1.87 |
| 20 | 54.8 ± 2.9 | 0.6 ± 0.01 | 29.5 ± 1.7 | 2.5 ± 0.07 | 15.7 ± 1.2 | 7.6 ± 0.02 | 0.98 | 1.8 |
| 30 | 49.8 ± 2.9 | 0.7 ± 0.08 | 34 ± 2.7 | 2.8 ± 0.3 | 16.2 ± 2.8 | 7.9 ± 0.32 | 1.031 | 1.92 |
| 40 | 45.3 ± 0.1 | 0.5 ± 0.1 | 37.7 ± 2.1 | 2.3 ± 0.2 | 17 ± 0.95 | 7.9 ± 0.1 | 1.002 | 1.94 |
| 50 | 34.9 ± 1.1 | 0.7 ± 0.1 | 45.2 ± 1.2 | 2.4 ± 0.3 | 19.9 ± 0.7 | 7.85 ± 0.5 | 0.954 | 1.81 |
| 60 | 28.8 ± 4.5 | 0.76 ± 0.2 | 50.1 ± 3.2 | 2.78 ± 0.4 | 21.1 ± 1.7 | 8 ± 0.6 | 0.97 | 2.01 |

TABLE 9

Time resolved fluorescence lifetimes from glycated alpha crystallin by excitation at 370 nm and emission maxima between 440-460 nm.

| Time of glycation with MGO (days) | Lifetimes, $\tau$ (ns) and Relative contributions at time zero, A (%) | | | | | | $\chi^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Control | 40.5 ± 1.8 | 1.1 ± 0.1 | 39.2 ± 0.1 | 3.6 ± 0.17 | 20.3 ± 2.6 | 10.1 ± 1.7 | 0.97 | 1.82 |
| 10 | 41.9 ± 1.4 | 1.2 ± 0.2 | 37.9 ± 0.01 | 3.7 ± 0.14 | 20.2 ± 0.6 | 10.6 ± 0.7 | 0.997 | 1.945 |
| 20 | 42.8 ± 2.9 | 1.3 ± 0.31 | 36.1 ± 1.6 | 3.67 ± 0.1 | 21.1 ± 0.7 | 10.5 ± 1.7 | 0.99 | 1.85 |
| 30 | 44.1 ± 0.3 | 1.16 ± 0.2 | 34.1 ± 0.2 | 3.55 ± 0.09 | 21.8 ± 0.6 | 10.6 ± 0.5 | 1.01 | 1.801 |
| 40 | 45.1 ± 0.2 | 1.2 ± 0.11 | 31.7 ± 0.31 | 3.6 ± 0.24 | 23.2 ± 0.01 | 10 ± 0.6 | 0.985 | 1.917 |
| 50 | 49.2 ± 0.2 | 1.0 ± 0.43 | 29.1 ± 0.3 | 3.6 ± 0.19 | 21.7 ± 2.7 | 10.7 ± 0.3 | 1.013 | 1.95 |
| 60 | 51.6 ± 0.2 | 1.1 ± 0.39 | 27.3 ± 0.64 | 3.4 ± 0.41 | 21.1 ± 0.3 | 10.6 ± 1.4 | 0.988 | 1.9 |

TABLE 10

Comparison of time resolved fluorescence lifetimes from 20 yr old non-diabetic and 18 yr old type I diabetic human donor lenses by excitation at 435 nm and emission maxima between 500-510 nm

| Type of donor lens | Lifetimes, $\tau$ (ns) and Relative contributions at time zero, A (%) | | | | | | $\chi^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Non-diabetic (20 yr) | — | — | — | — | — | — | — | — |
| Diabetic (18 yr) | — | — | 80.4 ± 0.01 | 4.7 ± 0.07 | 19.6 ± 0.1 | 16.9 ± 0.1 | 0.997 | 1.981 |

TABLE 11

Comparison of time resolved fluorescence lifetimes from 42 yr old non-diabetic and 42 yr old type II diabetic human donor lenses by excitation at 435 nm and emission maxima between 500-510 nm

| Type of donor lens | Lifetimes, $\tau$ (ns) and Relative contributions at time zero, A (%) | | | | | | $\chi^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Non-diabetic (42 yr) | — | — | — | — | — | — | — | — |
| Diabetic (42 yr) | — | — | 84.1 ± 2.2 | 4.2 ± 0.77 | 15.9 ± 3.2 | 17.1 ± 0.5 | 1.073 | 1.74 |

TABLE 12

Comparison of time resolved fluorescence lifetimes from donor lenses of 56 yr old non-diabetic and 56 yr old with diabetic retinopathy by excitation at 435 nm and emission maxima between 500-510 nm

| Type of donor lens | Lifetimes, $\tau$ (ns) and Relative contributions at time zero, A (%) | | | | | | $\chi^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Non-diabetic (56 yr) | — | — | 100 | 4.5 ± 0.17 | — | — | 1.07 | 1.79 |
| Diabetic (56 yr) | — | — | 51.4 ± 0.8 | 4.6 ± 0.11 | 48.6 ± 0.2 | 17 ± 0.17 | 1.073 | 1.74 |

TABLE 13

Comparison of time resolved fluorescence lifetimes from donor lenses of 64 yr old non-diabetic and 67 yr old with cataract by excitation at 435 nm and emission maxima between 500-510 nm

| Type of donor lens | Lifetimes, τ (ns) and Relative contributions at time zero, A (%) | | | | | | $x^2$ value | Durbin-Watson parameter |
|---|---|---|---|---|---|---|---|---|
| | $A_1$ | $\tau_1$ | $A_2$ | $\tau_2$ | $A_3$ | $\tau_3$ | | |
| Non-diabetic (64 yr) | — | — | 100 | 4.76 ± 0.1 | — | — | 0.992 | 1.86 |
| Diabetic (67 yr) | 39 ± 1.9 | 1.4 ± 0.2 | 41.9 ± 0.5 | 4.5 ± 0.3 | 20.1 ± 1.2 | 15.6 ± 0.9 | 1.073 | 1.94 |

---

The invention claimed is:

1. A method for diagnosing a disease or condition in a subject at an early stage to facilitate treatment by screening of the ocular lens of the subject at 435 nm, wherein the method comprises:
  (a) detecting an advanced glycation end-product fluorophores that formed in the α-crystallin of the ocular lens and surrounding tissue, using steady state and time resolved fluorescence in a sequential order and recording results;
  (b) quantifying the fluorophores formed on the α-crystallin to determine the fluorescence lifetimes of the fluorophores;
  (c) using the fluorescence lifetimes to distinguish between normal and pathological ocular lens and surrounding tissue; and
  (d) diagnosing the disease based on the presence of pathological ocular lens lifetimes in the subject.

2. The method of claim 1 wherein the disease or condition is diabetes or diabetic retinopathy.

3. The method of claim 1, wherein spectroscopic changes in the visible spectrum between 401-600 nm are based on fluorescence lifetimes with aging and pathological conditions in a small heat shock protein, α-crystallin and its subunits.

4. The method for diagnosing a disease or condition of claim 1, further defined as analyzing aging and pathological conditions in the eye.

5. The method of claim 1, wherein the fluorophores are advanced glycation endproducts (AGEs) when measured in vitro from the lens tissue sample and wherein in vivo, the fluorophores are a combination of advanced glycation end products formed on macromolecules in the eye.

6. The method of claim 5 wherein other fluorophores further are selected from the group consisting of A2E, lipofuscin, FAD and NADH.

7. The method of claim 1, wherein the disease diagnosed by screening the lens is based on quantifying two or more fluorescence lifetimes in the range of 1.6 to 17 ns.

8. The method of claim 1, wherein fluorophores in the eye are used for differential diagnosis.

* * * * *